US008759539B2

(12) United States Patent
He et al.

(10) Patent No.: US 8,759,539 B2
(45) Date of Patent: Jun. 24, 2014

(54) SUBSTITUTED BICYCLIC AMINES FOR THE TREATMENT OF DIABETES

(75) Inventors: Jiafang He, Dayton, NJ (US); John Bawiec, Wilkes-Barre, PA (US); Weiguo Liu, Princeton, NJ (US); Gui-Bai Liang, Scotch Plains, NJ (US); Lihu Yang, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 584 days.

(21) Appl. No.: 13/125,088

(22) PCT Filed: Nov. 11, 2009

(86) PCT No.: PCT/US2009/063988
§ 371 (c)(1),
(2), (4) Date: Apr. 20, 2011

(87) PCT Pub. No.: WO2010/056717
PCT Pub. Date: May 20, 2010

(65) Prior Publication Data
US 2011/0207737 A1   Aug. 25, 2011

Related U.S. Application Data

(60) Provisional application No. 61/115,161, filed on Nov. 17, 2008.

(51) Int. Cl.
| C07D 401/12 | (2006.01) |
| C07D 401/14 | (2006.01) |
| C07D 403/12 | (2006.01) |
| C07D 403/14 | (2006.01) |
| C07D 209/52 | (2006.01) |
| C07D 413/12 | (2006.01) |
| C07D 417/12 | (2006.01) |
| A61K 31/403 | (2006.01) |
| A61K 31/4184 | (2006.01) |
| A61K 31/4192 | (2006.01) |
| A61K 31/427 | (2006.01) |
| A61K 31/4709 | (2006.01) |
| A61K 31/4725 | (2006.01) |
| A61K 31/423 | (2006.01) |

(52) U.S. Cl.
USPC ........ 548/452; 548/455; 548/304.4; 548/261; 548/159; 548/222; 548/126; 546/277.4; 546/169; 546/275.4; 546/256; 546/274.1; 546/269.7; 546/152; 546/269.4; 544/335; 544/406; 544/405; 544/238; 544/235; 544/314; 544/3; 514/367; 514/375; 514/339; 514/255.05; 514/333; 514/314; 514/300; 514/364; 514/338; 514/273; 514/307; 514/412; 514/252.06; 514/248; 514/249; 514/394; 514/359; 514/414; 514/269

(58) Field of Classification Search
USPC .................................................. 548/515, 452
See application file for complete search history.

(56) References Cited

U.S. PATENT DOCUMENTS

| 7,232,879 B2 | 6/2007 | Galloway et al. |
| 2006/0205718 A1 | 9/2006 | Binggeli et al. |
| 2006/0287290 A1 | 12/2006 | Dart et al. |
| 2007/0032489 A1 | 2/2007 | Weintraub et al. |
| 2007/0093521 A1 | 4/2007 | Binggeli et al. |
| 2008/0064697 A1 | 3/2008 | Christ et al. |

FOREIGN PATENT DOCUMENTS

| WO | 2007/138431 A2 | 12/2007 |
| WO | 2007/138431 A3 | 12/2007 |

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*
International Search Report for U.S. Appl. No. 13/125,088, PCT/US/09/63988, Jan. 14, 2010.

* cited by examiner

*Primary Examiner* — Laura L. Stockton
(74) *Attorney, Agent, or Firm* — Janet E. Fair; Anna L. Cocuzzo

(57) ABSTRACT

Described herein are substituted bicyclic amines. In particular, described herein are substituted bicyclic amines that are effective as antagonists of SSTR5 and useful for the treatment, control or prevention of disorders responsive to antagonism of SSTR5, such as type 2 diabetes, insulin resistance, lipid disorders, obesity, atherosclerosis, metabolic syndrome, depression, and anxiety.

12 Claims, No Drawings

SUBSTITUTED BICYCLIC AMINES FOR THE TREATMENT OF DIABETES

CROSS-REFERENCE TO RELATED APPLICATIONS

This application is a U.S. National Phase application under 35 U.S.C. §371 of PCT Application No. PCT/US2009/063988, filed Nov. 11, 2009, which published as WO 2010/056717 A1 on May 20, 2010, and claims priority under 35 U.S.C. §365(b) from U.S. patent application No. 61/115,161, filed Nov. 17, 2008.

FIELD OF THE INVENTION

Described herein are substituted bicyclic amines. In particular, described herein are substituted bicyclic amines that are effective as antagonists of the somatostatin receptor subtype 5 (SSTR5) and useful for the treatment, control or prevention of disorders responsive to antagonism of SSTR5, such as type 2 diabetes, insulin resistance, lipid disorders, obesity, atherosclerosis, metabolic syndrome, depression, and anxiety.

BACKGROUND

Diabetes mellitus is a disease derived from multiple causative factors and characterized by elevated levels of plasma glucose (hyperglycemia) in the fasting state, the postprandial state, or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced by islet cells in the pancreas. Patients having type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, Int. J. Obes. Relat. Metab. Disord. 24 Suppl 2:S29-31 (2000)). The beta cells within the pancreatic islets initially compensate for insulin resistance by increasing insulin output. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the onset of type 2 diabetes due to insufficient increases (or actual declines) in beta cell mass is apparently due to increased beta cell apoptosis relative to non-diabetic insulin resistant individuals (Butler et al., Diabetes, 52, 102-110 (2003)).

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or metabolic syndrome. According to one widely used definition, a patient having metabolic syndrome is characterized as having three or more symptoms selected from the following group of five symptoms: (1) abdominal obesity, (2) hypertriglyceridemia, (3) low levels of high-density lipoprotein cholesterol (HDL), (4) high blood pressure, and (5) elevated fasting glucose, which may be in the range characteristic of type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether they have or develop overt diabetes mellitus, have an increased risk of developing the macrovascular and microvascular complications that occur with type 2 diabetes, such as atherosclerosis and coronary heart disease.

There are several available treatments for type 2 diabetes, each of which has its own limitations and potential risks. Physical exercise and a reduction in dietary intake of calories often dramatically improves the diabetic condition and are the usual recommended first-line treatment of type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments have largely focused on the following areas of pathophysiology: (1) hepatic glucose production (biguanides), (2) insulin resistance (PPAR agonists), (3) insulin secretion (sulfonylureas); (4) incretin hormone mimetics (GLP-1 derivatives and analogs, such as exenatide and luraglitide); and (5) inhibitors of incretin hormone degradation (DPP-4 inhibitors). Each treatment has its own strengths and weaknesses.

Additional research has focused on pancreatic islet-based insulin secretion that is controlled by glucose-dependent insulin secretion. This approach has the potential for stabilization and restoration of β-cell function. In this regard, research has been done on the affects of antagonizing one or more of the somatostatin receptors. Somatostatin (SST) is a cyclic tetradecapeptide hormone that is widely distributed throughout the body and exhibits multiple biological functions that are mostly inhibitory in function, such as the release of growth hormone, pancreatic insulin, glucagon, and gastrin.

SST hormone activity is mediated through SST-14 and SST-28 isoforms that differentially bind to the five different SST receptor subtypes (SSTR1-5). In humans SSTR1 and SSTR2 are found in the pituitary, small intestine, heart and spleen with SSTR2 predominately in the pancreas, pituitary and the stomach. SSTR3 and SSTR4 are found in the pituitary, heart, liver, spleen stomach, small intestine and kidney. SSTR5 is found in high concentration in the pituitary, as well as the pancreas. It has been shown that S-28 and S-14 bind with similar affinity to SSTR1, SSTR2, SSTR3, and SSTR4. The receptor SSTR5 can be characterized by its preferential affinity for S-28 (Chisholm et al., Am. J. Physiol Endocrinol Metab. 283:E311-E317 (2002)).

SSTR5 is expressed by human islet β cells that are responsible for producing insulin and amylin. Thus, binding to the SSTR5 could affect insulin secretion. For example, by using in vitro isolated perfused pancreas preparations from 3-month-old mice, it was demonstrated that SSTR5 global knockout mice pancreata have low basal insulin production, but a near normal response to glucose stimulation. It was theorized that, since along with SSTR5, SSTR1 is also expressed in islet β cells up-regulated SSTR1 compensates for the loss of SSTR5 in young knockout mice. As the mice aged, however, SSTR1 expression decreased in both the knockout mice and the aged-control wild-type mice. With lower SSTR1 expression in vivo, SSTR5 knockout mice had increased basal and glucose stimulated insulin secretion due to near complete lack of SSTRs on the knockout mice islet β cells with subsequent loss of the inhibitory SST response (Wang et al., Journal of Surgical Research, 129, 64-72 (2005)).

The proximity of D cells producing S-28 and L-cells containing GLP-1 in the ileum suggest that S-28 acting through SSTR5 may additionally participate in the direct regulation of GLP-1 secretion. To determine if S-28 acting through SSTR5 participates in the direct regulation of GLP-1 secretion, fetal rat intestinal cell cultures were treated with somatostatin analogs with relatively high specificity for SSTR2-5. GLP-1 secretion was inhibited by an SSTR5-selective analog more potently that S-14 and nearly as effectively as S-28 (Chisholm et al., Am. J. Physiol Endocrinol Metab. 283:E311-E317, 2002). A selective antagonist of SSTR5 is anticipated to block the suppression of GLP-1 secretion by endogenous somatostatin peptides, thereby elevating circulating GLP-1 levels. Elevated endogenous GLP-1 levels are associated with beneficial effects in the treatment of type 2 diabetes (Arulmozhi et al., European Journal of Pharmaceutical Sciences, 28, 96-108 (2006)).

Thus, described herein are selective, directly acting SSTR5 antagonists, which are useful as therapeutically active agents for the treatment and/or prevention of diseases that are associated with the modulation of SSTR5. Such diseases that can be treated or prevented with SSTR5 antagonists include diabetes mellitus, impaired glucose tolerance and elevated fasting glucose.

SUMMARY

Described herein are compounds of structural formula I:

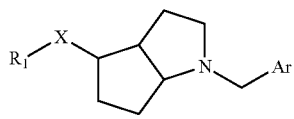

and pharmaceutically acceptable salts thereof. The substituted bicyclic amines described herein are effective antagonists of somatostatin receptors subtype 5 (SSTR5) and are useful for the treatment, control or prevention of disorders responsive to antagonism of SSTR5, such as type 2 diabetes, insulin resistance, lipid disorders, obesity, atherosclerosis, metabolic syndrome, depression, and anxiety.

Also described herein, are compositions comprising the compounds described herein and a pharmaceutically acceptable carrier.

Also described herein are compositions comprising the compounds described herein for the treatment, control, or prevention of disorders, diseases, or conditions responsive to antagonism of SSTR5 in a subject in need thereof.

Also described herein, are compositions comprising the compounds described herein for the treatment, control, or prevention of type 2 diabetes, hyperglycemia, insulin resistance, obesity, lipid disorders, atherosclerosis, and metabolic syndrome.

Also described herein, are compositions comprising the compounds described herein for the enhancement of GLP-1 secretion.

Also described herein, are compositions comprising the compounds described herein and a therapeutically effective amount of another agent, for the treatment of diabetes.

Also described herein, are methods for the treatment, control, or prevention of disorders, diseases, or conditions responsive to antagonism of SSTR5 in a subject in need thereof by administering the compounds and pharmaceutical compositions described herein.

Also described herein, are methods for the treatment, control, or prevention of type 2 diabetes, hyperglycemia, insulin resistance, obesity, lipid disorders, atherosclerosis, and metabolic syndrome by administering, to a mammal, the compounds and pharmaceutical compositions described herein.

Also described herein, are methods of enhancing GLP-1 secretion in a mammal by administering, to a mammal, the compounds and pharmaceutical compositions described herein.

Also described herein, are methods for the treatment, control, or prevention of diabetes by administering the compounds described herein in combination with a therapeutically effective amount of another agent known to be useful to treat the condition.

Also described herein, are methods for the treatment, control, or prevention of type 2 diabetes by administering the compounds described herein in combination with a therapeutically effective amount of another agent known to be useful to treat the type 2 diabetes.

Also described herein are uses of the compounds described herein in the manufacture of a medicament for the treatment, control or prevention of disorders, diseases, or conditions responsive to antagonism of SSTR5.

Also described herein are uses of the compounds described herein in the manufacture of a medicament for the treatment, control or prevention of type 2 diabetes, hyperglycemia, insulin resistance, obesity, lipid disorders, atherosclerosis, and metabolic syndrome.

Also described herein are uses of the compounds described herein in the manufacture of a medicament for the suppression of GLP-1 secretion in a mammal.

Also described herein are uses of the compounds described herein in the manufacture of a medicament that also includes a therapeutically effective amount of another agent for the treatment of diabetes.

DETAILED DESCRIPTION

Compounds

Described herein are compounds of structural formula I:

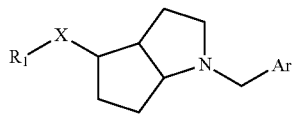

or a pharmaceutically acceptable salt thereof; wherein

Ar is an aryl or heteroaryl, wherein the aryl or heteroaryl is optionally substituted with one or more substituents independently selected from the group consisting of
(1) —$OC_{1-10}$ alkyl,
(2) —$OC_{3-6}$ cycloalkyl,
(3) —O-heteroaryl,
(4) —O-aryl,
(5) aryl,
(6) aryl substituted with one to three halogen,
(7) aryl substituted with one to three $C_{1-10}$ alkyl,
(8) heteroaryl,
(9) heteroaryl substituted with one to three halogen,
(10) heteroaryl substituted with one to three $C_{1-10}$ alkyl,
(11) halogen,
(12) oxo,
(13) —$CO_2H$,
(14) —$C_{1-10}$ alkoxycarbonyl,
(15) —CN,
(16) —$CF_3$,
(17) $NH_2$
(18) pyrrolidone,
(19) cycloheteroalkyl,
(20) $C_{1-10}$ alkyl,
(21) $C_{3-6}$ cycloalkyl, and
(22) $C_{3-6}$ cycloalkyl substituted with one to three $C_{1-10}$ alkyl;

X is O, NH or $OCH_2$;

$R^1$ is $SO_2H$, CONH, CONH$C_{1-10}$ alkyl, —$C_{1-10}$ alkoxycarbonyl, aroyl, heteroaroyl, aryl, heteroaryl, cycloalkyl or cycloheteroalkyl wherein the CONH, CONH$C_{1-10}$ alkyl, —$C_{1-10}$ alkoxycarbonyl, aroyl, heteroaroyl, aryl, heteroaryl, cycloalkyl or cycloheteroalkyl are optionally substituted with one or more substituents independently selected from the group consisting of:
(1) —OH,
(2) —$OC_{1-10}$ alkyl,
(3) —$OC_{3-6}$ cycloalkyl,
(4) —O-heteroaryl,
(5) —O-aryl,
(6) aryl substituted with one to three halogen,
(7) aryl,
(8) aryl substituted with one to three $C_{1-10}$ alkyl,
(9) heteroaryl,
(10) halogen,
(11) —$SO_2C_{1-10}$ alkyl,
(12) —$SO_2$-aryl,
(13) —$SO_2$-aryl-$C_{1-10}$alkyl,
(14) —$NSO_2C_{1-10}$ alkyl,
(15) —$NSO_2$-aryl,
(16) —$NSO_2$-aryl-$C_{1-10}$alkyl,
(17) —C(O)H,
(18) —C(O)$C_{1-10}$ alkyl,
(19) —C(O)$C_{3-6}$ cycloalkyl,
(20) —C(O) cycloalkyl,
(21) —C(O) heteroaryl,
(22) —C(O) aryl,
(23) —OC(O)H,
(24) —OC(O)$C_{1-10}$ alkyl,
(25) —OC(O)$C_{3-6}$ cycloalkyl,
(26) —OC(O) cycloalkyl,
(27) —OC(O) heteroaryl,
(28) —OC(O) aryl,
(29) oxo,
(30) —$NH_2$,
(31) —CONN—$C_{1-10}$ alkyl-aryl,
(32) —$CONH_2$,
(33) —$NO_2H$,
(34) —$CO_2H$,
(35) —$C_{1-10}$ alkoxycarbonyl,
(36) —$CO_2C_{1-10}$ alkylaryl,
(37) —CN,
(38) —$CF_3$,
(39) —$OCF_3$,
(40) —$OCHF_2$,
(41) cycloheteroalkyl,
(42) $C_{1-10}$ alkyl-OH,
(43) $C_{1-10}$ alkyl, and
(44) $C_{3-6}$ cycloalkyl.

In certain embodiments described herein, Ar is an unsubstituted aryl or heteroaryl. In other embodiments described herein, Ar is a substituted aryl or heteroaryl. In still other embodiments described herein, Ar is an unsubstituted aryl. In other embodiments described herein, Ar is a substituted aryl. In still other embodiments described herein, Ar is an unsubstituted heteroaryl. In other embodiments described herein, Ar is a substituted heteroaryl. For example, in some embodiments, Ar is phenyl, pyrrole, isoxazole, isothiazole, pyrazole, pyridine, oxazole, oxadiazole, thiadiazole, thiazole, imidazole, triazole, tetrazole, furan, triazine, thiene, pyrimidine, benzisoxazole, benzoxazole, benzothiazole, benzothiadiazole, dihydrobenzofuran, indoline, pyridazine, indazole, isoindole, dihydrobenzothiene, indolizine, cinnoline, phthalazine, quinazoline, naphthyridine, carbazole, benzodioxole, quinoxaline, purine, furazan, isobenzylfuran, benzimidazole, benzofuran, benzothiene, quinole, indole, isoquinole or dibenzofuran. In certain embodiments, Ar is phenyl.

In certain embodiments described herein, Ar is a substituted aryl or heteroaryl, wherein the aryl or heteroaryl are substituted with one or more substituents independently selected from the group consisting of:
(1) —$OC_{1-10}$ alkyl,
(2) —$OC_{3-6}$ cycloalkyl,
(3) —O-heteroaryl,
(4) —O-aryl,
(5) aryl,
(6) aryl substituted with one to three halogen,
(7) aryl substituted with one to three $C_{1-10}$ alkyl,
(8) heteroaryl,
(9) halogen,
(10) oxo,
(11) —$CO_2H$,
(12) —$C_{1-10}$ alkoxycarbonyl,
(13) —CN,
(14) —$CF_3$,
(15) pyrrolidone,
(16) cycloheteroalkyl,
(17) $C_{1-10}$ alkyl,
(18) $C_{3-6}$ cycloalkyl, and
(19) $C_{3-6}$ cycloalkyl substituted with one to three $C_{1-10}$ alkyl.

In certain embodiments described herein, Ar is a substituted or unsubstituted aryl, wherein the aryl is optionally substituted with one or more substituents independently selected from the group consisting of:
(1) —$OC_{1-10}$ alkyl,
(2) —$OC_{3-6}$ cycloalkyl,
(3) —O heteroaryl,
(4) —O aryl,
(5) aryl
(6) aryl substituted with one to three halogen,
(7) aryl substituted with one to three $C_{1-10}$ alkyl,
(8) heteroaryl,
(9) halogen,
(10) oxo,
(11) —$CO_2H$,
(12) alkoxycarbonyl,
(13) —CN,
(14) —$CF_3$,
(15) pyrrolidone,
(16) cycloheteroalkyl,
(17) $C_{1-10}$ alkyl,
(18) $C_{3-6}$ cycloalkyl, and
(19) $C_{3-6}$ cycloalkyl substituted with one to three $C_{1-10}$ alkyl.

In certain embodiments described herein, Ar is a substituted or unsubstituted aryl, wherein the aryl is optionally substituted with one or more substituents independently selected from the group consisting of:
(1) $CO_2H$,
(2) —$OC_{1-10}$ alkyl,
(3) aryl substituted with one to three halogen,
(4) heteroaryl,
(5) aryl,
(6) aryl substituted with one to three $C_{1-10}$ alkyl,
(7) $C_{1-10}$ alkyl, and
(8) $C_{3-6}$ cycloalkyl.

In certain embodiments described herein, X is O, NH or $OCH_2$. In other embodiments described herein X is O or NH. In still other embodiments described herein, X is NH. In still other embodiments described herein, X is O.

In certain embodiments described herein, $R^1$ is $SO_2H$, CONN, CONH$C_{1-10}$ alkyl, $C_{1-10}$ alkoxycarbonyl, aroyl, heteroaroyl, aryl, heteroaryl, cycloalkyl or cycloheteroalkyl. In other embodiments described herein, $R^1$ is aroyl, heteroaroyl, aryl, heteroaryl, cycloalkyl or cycloheteroalkyl. In still other embodiments described herein, $R^1$ is aroyl or heteroaroyl. Additionally, in certain embodiments, $R^1$ is substituted or unsubstituted.

In still other embodiments described herein, $R^1$ is selected from the group consisting of:

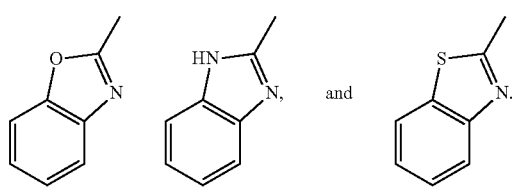

In still other embodiments described herein, $R^1$ is selected from the group consisting of:

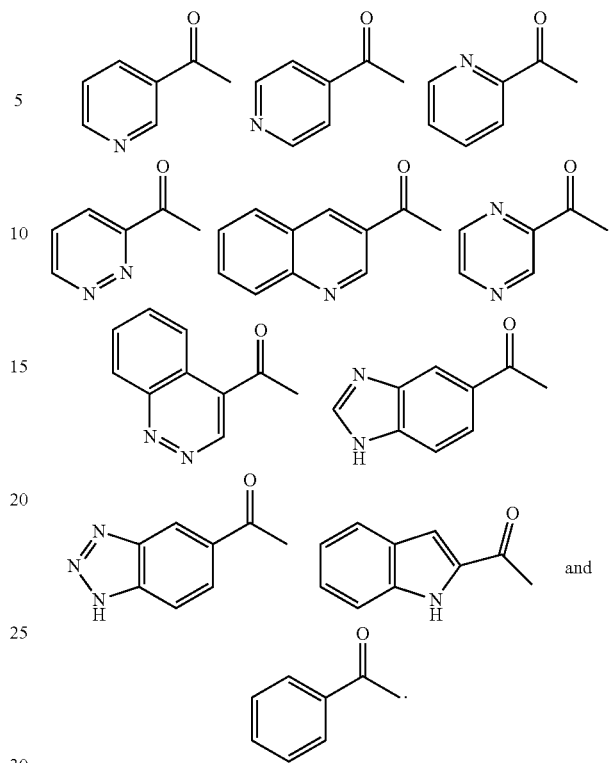

In certain embodiments described herein, $R^1$ is substituted with one or more substituents from the group consisting of
(1) —OH,
(2) —$OC_{1-10}$ alkyl,
(3) —$OC_{3-6}$ cycloalkyl,
(4) —O-heteroaryl,
(5) —O-aryl,
(6) aryl substituted with one to three halogen,
(7) aryl,
(8) aryl substituted with one to three $C_{1-10}$ alkyl,
(9) heteroaryl,
(10) halogen,
(11) —$SO_2C_{1-10}$ alkyl,
(12) —$SO_2$-aryl,
(13) —$SO_2$-aryl-$C_{1-10}$alkyl,
(14) —$NSO_2C_{1-10}$ alkyl,
(15) —$NSO_2$-aryl,
(16) —$NSO_2$-aryl-$C_{1-10}$alkyl,
(17) —C(O)H,
(18) —C(O)$C_{1-10}$ alkyl,
(19) —C(O)$C_{3-6}$ cycloalkyl,
(20) —C(O) cycloalkyl,
(21) —C(O) heteroaryl,
(22) —C(O) aryl,
(23) —OC(O)H,
(24) —OC(O)$C_{1-10}$ alkyl,
(25) —OC(O)$C_{3-6}$ cycloalkyl,
(26) —OC(O) cycloalkyl,
(27) —OC(O) heteroaryl,
(28) —OC(O) aryl,
(29) oxo,
(30) —$NH_2$,
(31) —CONN—$C_{1-10}$ alkyl-aryl,
(32) —$CONH_2$,
(33) —$NO_2H$,

(34) —CO$_2$H,
(35) —C$_{1-10}$ alkoxycarbonyl,
(36) —CO$_2$C$_{1-10}$ alkylaryl,
(37) —CN,
(38) —CF$_3$,
(39) —OCF$_3$,
(40) —OCHF$_2$,
(41) cycloheteroalkyl,
(42) C$_{1-10}$ alkyl-OH,
(43) C$_{1-10}$ alkyl, and
(44) C$_{3-6}$ cycloalkyl.

In certain embodiments described herein, R$^1$ is substituted with one or more substituents from the group consisting of:
(1) aryl substituted with one to three halogen,
(2) heteroaryl,
(3) C$_{3-6}$ cycloalkyl,
(4) cycloheteroalkyl,
(5) —OC$_{1-10}$ alkyl,
(6) halogen,
(7) —SO$_2$C$_{1-10}$ alkyl,
(8) —NSO$_2$-aryl,
(9) —NSO$_2$-aryl-C$_{1-10}$alkyl,
(10) —NH$_2$,
(11) —CONH$_2$,
(12) —NO$_2$H,
(13) —CO$_2$H,
(14) —C$_{1-10}$ alkoxycarbonyl,
(15) —CO$_2$C$_{1-10}$ alkylaryl,
(16) —CF$_3$,
(17) —OCHF$_2$,
(18) C$_{1-10}$ alkyl-OH, and
(19) C$_{1-10}$ alkyl.

In certain embodiments described herein, R$^1$ is substituted with one or more substituents from the group consisting of:
(1) —OC$_{1-10}$ alkyl,
(2) halogen,
(3) —SO$_2$C$_{1-10}$ alkyl,
(4) —NSO$_2$-aryl,
(5) —NSO$_2$-aryl-C$_{1-10}$alkyl,
(6) —NH$_2$,
(7) —CONH$_2$,
(8) —NO$_2$H,
(9) —CO$_2$H,
(10) —C$_{1-10}$ alkoxycarbonyl,
(11) —CO$_2$C$_{1-10}$ alkylaryl,
(12) —CF$_3$,
(13) —OCHF$_2$,
(14) C$_{1-10}$ alkyl-OH, and
(15) C$_{1-10}$ alkyl.

Described herein are also compounds of structural formula Ia:

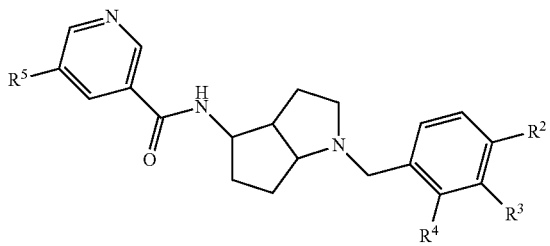

Ia or a pharmaceutically acceptable salt thereof; wherein R$^2$, R$^3$, R$^4$ and R$^5$ are independently selected from the group consisting of:
(1) —OH,
(2) —OC$_{t-10}$ alkyl,
(3) —OC$_{3-6}$ cycloalkyl,
(4) —O-heteroaryl,
(5) —O-aryl
(6) aryl substituted with one to three halogen,
(7) heteroaryl,
(8) halogen,
(9) —C(O)H,
(10) —C(O)C$_{1-10}$ alkyl,
(11) —C(O)C$_{3-6}$ cycloalkyl,
(12) —C(O) cycloalkyl,
(13) —C(O) heteroaryl,
(14) —C(O) aryl,
(15) —OC(O)H,
(16) —OC(O)C$_{1-10}$ alkyl,
(17) —OC(O)C$_{3-6}$ cycloalkyl,
(18) —OC(O) cycloalkyl,
(19) —OC(O) heteroaryl,
(20) —OC(O) aryl,
(21) oxo,
(22) —CO$_2$H,
(23) —C$_{1-10}$alkoxycarbonyl,
(24) —CN,
(25) —CF$_3$,
(26) —OCF$_3$,
(27) —OCHF$_2$,
(28) cycloheteroalkyl,
(29) C$_{1-10}$ alkyl, and
(30) C$_{3-6}$ cycloalkyl.

Described herein are also compounds of structural formula Ib:

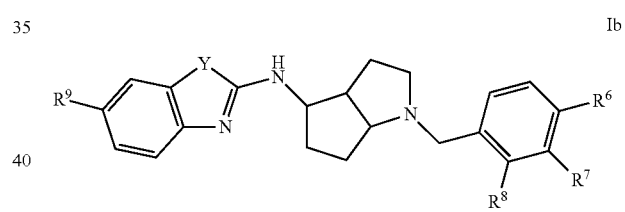

Ib or a pharmaceutically acceptable salt thereof; wherein R$^6$, R$^7$, R$^8$ and R$^9$ are independently selected from the group consisting of:
(1) —OH,
(2) —OC$_{1-10}$ alkyl,
(3) —OC$_{3-6}$ cycloalkyl,
(4) —O heteroaryl,
(5) —O aryl,
(6) aryl substituted with one to three halogen,
(7) heteroaryl,
(8) halogen,
(9) —C(O)H,
(10) —C(O)C$_{1-10}$ alkyl,
(11) —C(O)C$_{3-6}$ cycloalkyl,
(12) —C(O) cycloalkyl,
(13) —C(O) heteroaryl,
(14) —C(O) aryl,
(15) —OC(O)H,
(16) —OC(O)C$_{1-10}$ alkyl,
(17) —OC(O)C$_{3-6}$ cycloalkyl,
(18) —OC(O) cycloalkyl,
(19) —OC(O) heteroaryl,
(20) —OC(O) aryl,
(21) oxo,

(22) —CO₂H,
(23) —C$_{1-10}$ alkoxycarbonyl,
(24) —CN,
(25) —CF$_3$,
(26) —OCF$_3$,
(27) —OCHF$_2$,
(28) cycloheteroalkyl,
(29) C$_{1-10}$ alkyl, and
(30) C$_{3-6}$ cycloalkyl; and
wherein Y is O, S or N.

In certain embodiments, R$^6$, R$^7$, R$^8$ and R$^9$ are independently selected from the group consisting of
(1) —OH,
(2) —OC$_{1-10}$ alkyl,
(3) —OC$_{3-6}$ cycloalkyl,
(4) —O heteroaryl,
(5) —O aryl,
(6) aryl substituted with one to three halogen,
(7) heteroaryl; and
(8) halogen.

In certain embodiments, R$^6$, R$^7$ and R$^8$ are independently selected from the group consisting of:
(1) —OC$_{1-10}$ alkyl; and
(2) aryl substituted with one to three halogen.

In certain embodiments, R$^9$ is independently selected from the group consisting of:
(1) —OH,
(2) —OC$_{1-10}$ alkyl,
(3) —OC$_{3-6}$ cycloalkyl,
(4) —O heteroaryl,
(5) —O aryl,
(6) aryl substituted with one to three halogen,
(7) heteroaryl,
(8) halogen,
(9) —C(O)H,
(10) —C(O)C$_{1-10}$ alkyl,
(11) —C(O)C$_{3-6}$ cycloalkyl,
(12) —C(O) cycloalkyl,
(13) —C(O) heteroaryl,
(14) —C(O) aryl,
(15) —OC(O)H,
(16) —OC(O)C$_{1-10}$ alkyl,
(17) —OC(O)C$_{3-6}$ cycloalkyl,
(18) —OC(O) cycloalkyl,
(19) —OC(O) heteroaryl,
(20) —OC(O) aryl,
(21) oxo,
(22) —CO₂H,
(23) —C$_{1-10}$ alkoxycarbonyl,
(24) —CN,
(25) —CF$_3$,
(26) —OCF$_3$,
(27) —OCHF$_2$,
(28) cycloheteroalkyl,
(29) C$_{1-10}$ alkyl; and
(30) C$_{3-6}$ cycloalkyl.

Examples of the compounds described herein are listed in Table 1 and include:

TABLE 1

| EXAMPLE | COMPOUND |
|---|---|
| 1 | |
| 2 | |
| 3 | |
| 4 | |

TABLE 1-continued
| EXAMPLE | COMPOUND |
|---|---|
| 5 | 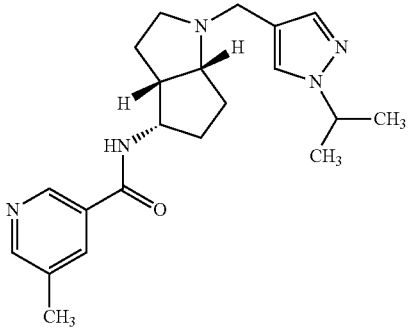 [SMILES: Cc1cncc(C(=O)N[C@H]2CC[C@@H]3[C@H]2CCN3Cc2cnn(C(C)C)c2)c1] |
| 6 | 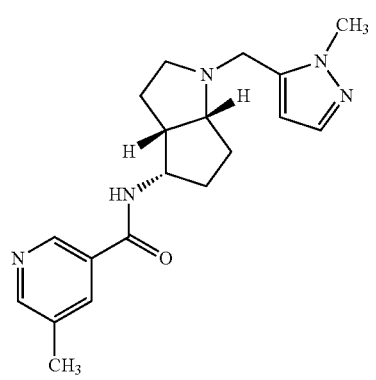 [SMILES: Cc1cncc(C(=O)N[C@H]2CC[C@@H]3[C@H]2CCN3Cc2ccnn2C)c1] |
| 7 | 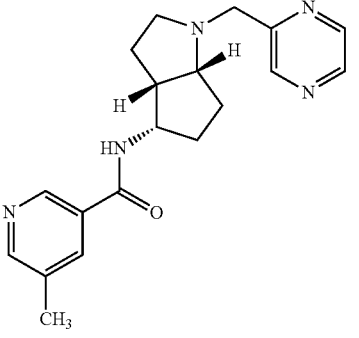 [SMILES: Cc1cncc(C(=O)N[C@H]2CC[C@@H]3[C@H]2CCN3Cc2cnccn2)c1] |
| 8 | 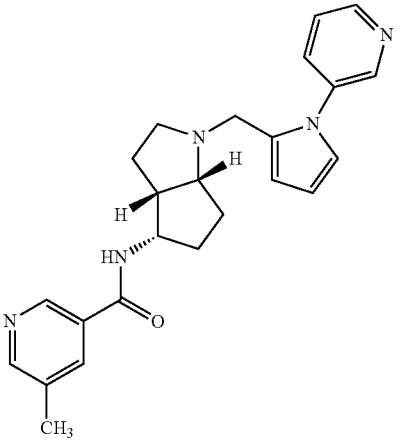 [SMILES: Cc1cncc(C(=O)N[C@H]2CC[C@@H]3[C@H]2CCN3Cc2cccn2-c2cccnc2)c1] |

TABLE 1-continued

| EXAMPLE | COMPOUND |
|---|---|
| 9 | |
| 10 | |
| 11 | |
| 12 | |

TABLE 1-continued

| EXAMPLE | COMPOUND |
| --- | --- |
| 13 | |
| 14 | |
| 15 | |
| 16 | |

TABLE 1-continued

| EXAMPLE | COMPOUND |
|---|---|
| 17 | |
| 18 | |
| 19 | |
| 20 | |

TABLE 1-continued
| EXAMPLE | COMPOUND |
|---|---|
| 21 | 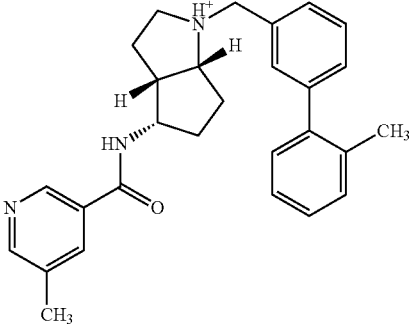 |
| 22 | 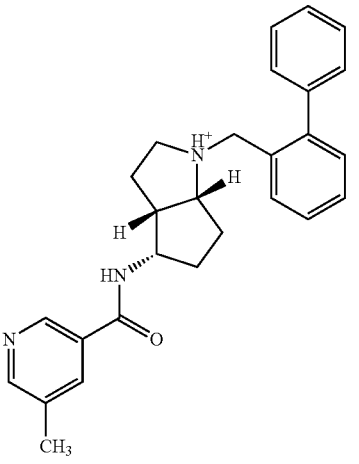 |
| 23 | 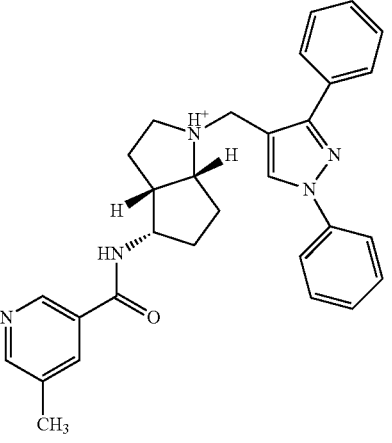 |
| 24 | 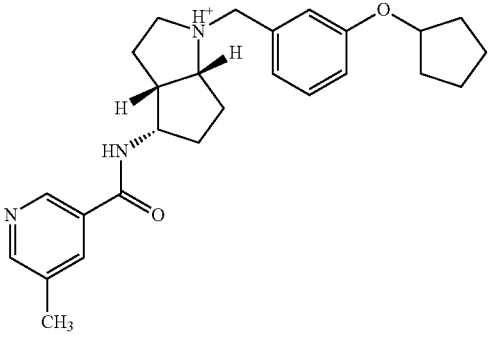 |

TABLE 1-continued
| EXAMPLE | COMPOUND |
|---|---|
| 25 | 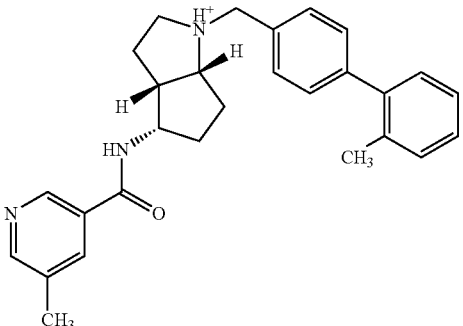 |
| 26 | 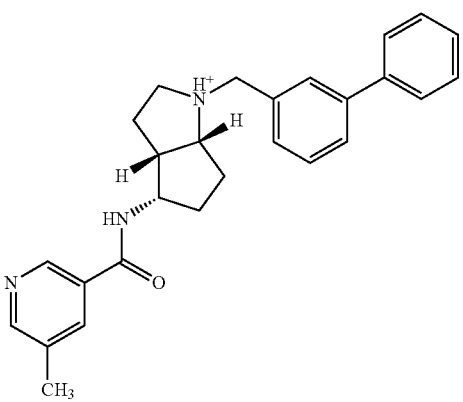 |
| 27 | 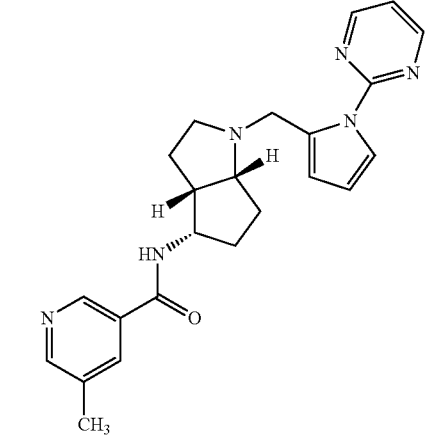 [SMILES: Cc1cncc(C(=O)N[C@H]2CC[C@@H]3[C@H]2CCN3Cc2cccn2-c2ncccn2)c1] |
| 28 | 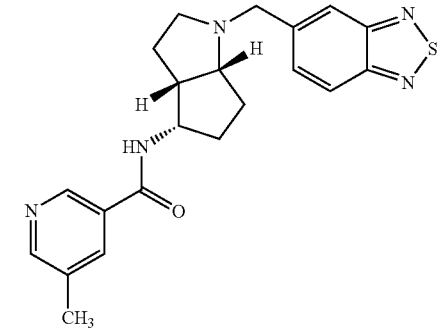 |

TABLE 1-continued
| EXAMPLE | COMPOUND |
|---|---|
| 29 | 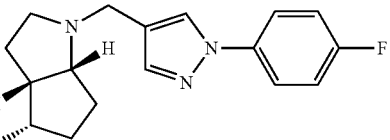 |
| 30 | 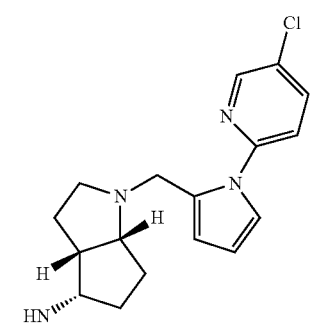 |
| 31 | 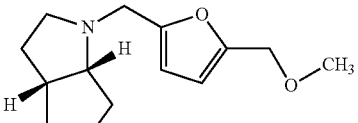 |
| 32 | 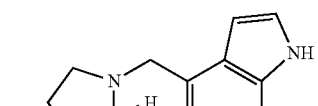 |

TABLE 1-continued
| EXAMPLE | COMPOUND |
| --- | --- |
| 33 | 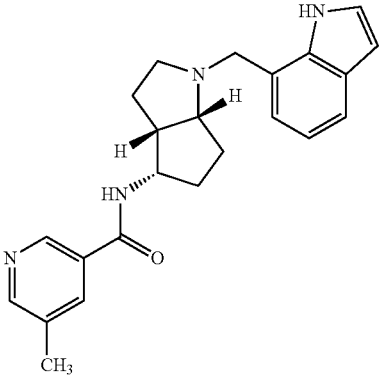 [SMILES: Cc1cncc(C(=O)N[C@H]2CC[C@@H]3[C@H]2CCN3Cc2cccc3cc[nH]c23)c1] |
| 34 | 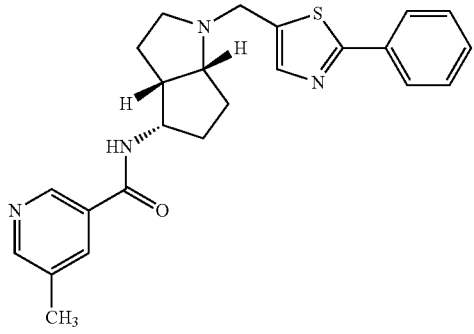 [SMILES: Cc1cncc(C(=O)N[C@H]2CC[C@@H]3[C@H]2CCN3Cc2cnc(-c3ccccc3)s2)c1] |
| 35 | 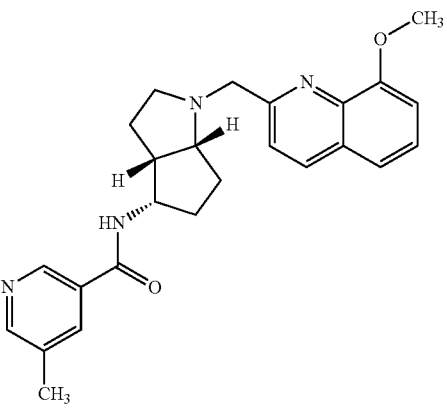 [SMILES: COc1cccc2ccc(CN3CC[C@H]4[C@@H](NC(=O)c5cncc(C)c5)CC[C@H]43)nc12] |
| 36 | 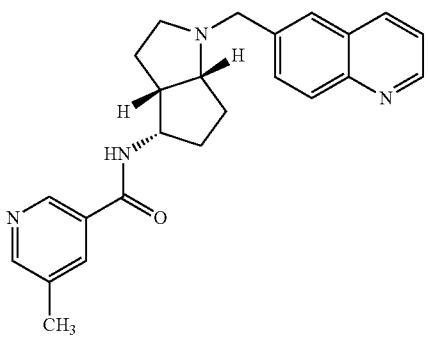 [SMILES: Cc1cncc(C(=O)N[C@H]2CC[C@@H]3[C@H]2CCN3Cc2ccc3ncccc3c2)c1] |

TABLE 1-continued

| EXAMPLE | COMPOUND |
|---|---|
| 37 | |
| 38 | |
| 39 | |
| 40 | |

TABLE 1-continued
| EXAMPLE | COMPOUND |
|---|---|
| 41 | 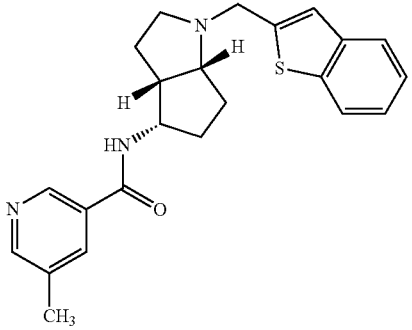 [SMILES: Cc1cncc(C(=O)N[C@H]2CC[C@@H]3[C@H]2CCN3Cc2cc3ccccc3s2)c1] |
| 42 | 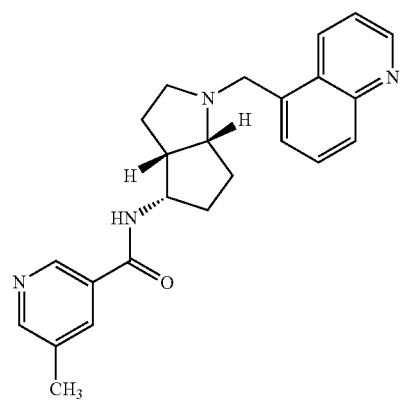 [SMILES: Cc1cncc(C(=O)N[C@H]2CC[C@@H]3[C@H]2CCN3Cc2cccc3ncccc23)c1] |
| 43 | 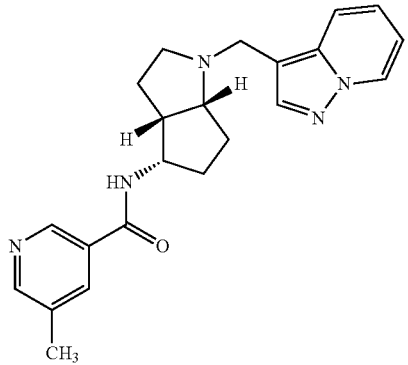 [SMILES: Cc1cncc(C(=O)N[C@H]2CC[C@@H]3[C@H]2CCN3Cc2cnn3ccccc23)c1] |
| 44 | 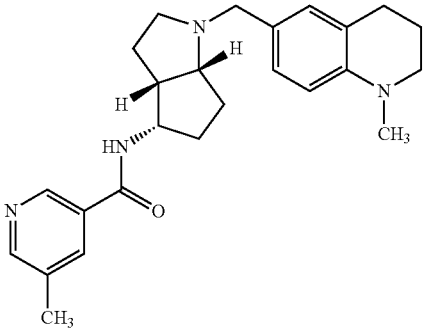 [SMILES: Cc1cncc(C(=O)N[C@H]2CC[C@@H]3[C@H]2CCN3Cc2ccc3c(c2)CCCN3C)c1] |

TABLE 1-continued
| EXAMPLE | COMPOUND |
|---|---|
| 45 | 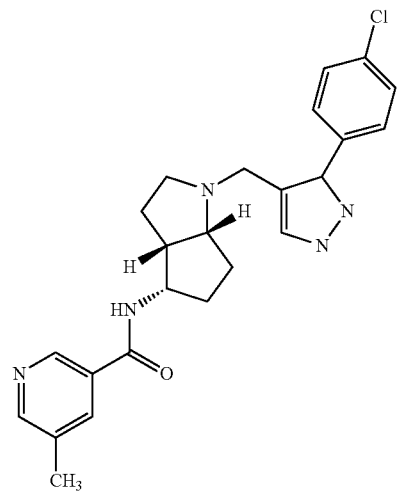 [SMILES: Cc1cncc(C(=O)N[C@H]2CC[C@@H]3[C@H]2CCN3CC2=CNNC2c2ccc(Cl)cc2)c1] |
| 46 | 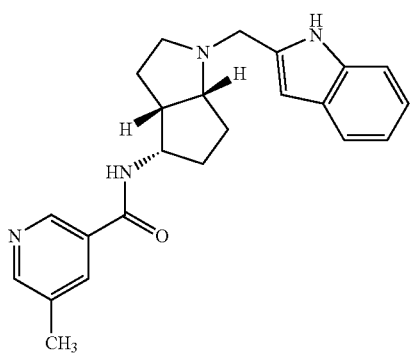 [SMILES: Cc1cncc(C(=O)N[C@H]2CC[C@@H]3[C@H]2CCN3Cc2cc3ccccc3[nH]2)c1] |
| 47 | 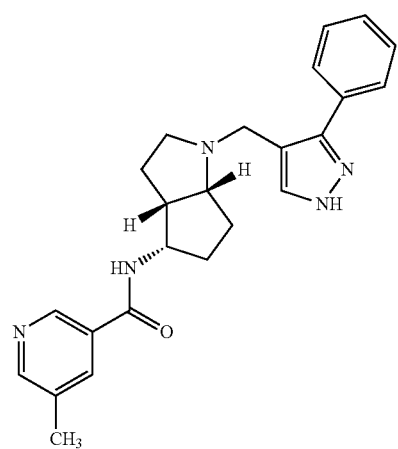 [SMILES: Cc1cncc(C(=O)N[C@H]2CC[C@@H]3[C@H]2CCN3Cc2c[nH]nc2-c2ccccc2)c1] |

TABLE 1-continued
| EXAMPLE | COMPOUND |
|---|---|
| 48 | 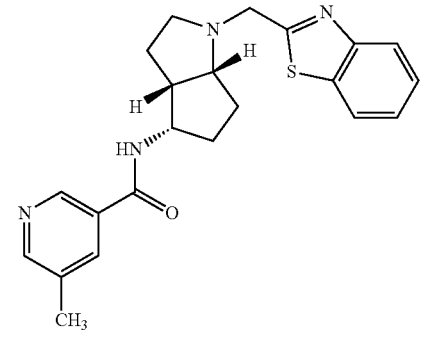 [SMILES: Cc1cncc(C(=O)N[C@H]2CC[C@@H]3[C@H]2CCN3Cc2nc3ccccc3s2)c1] |
| 49 | 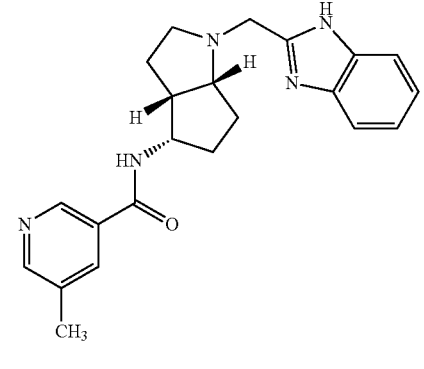 [SMILES: Cc1cncc(C(=O)N[C@H]2CC[C@@H]3[C@H]2CCN3Cc2nc3ccccc3[nH]2)c1] |
| 50 | 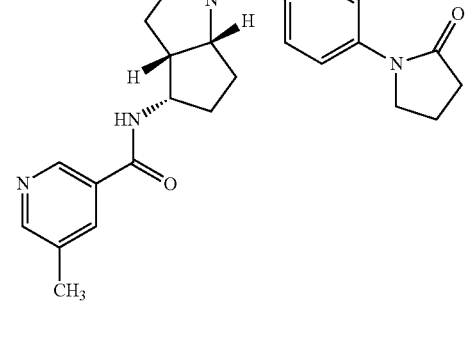 |
| 51 | 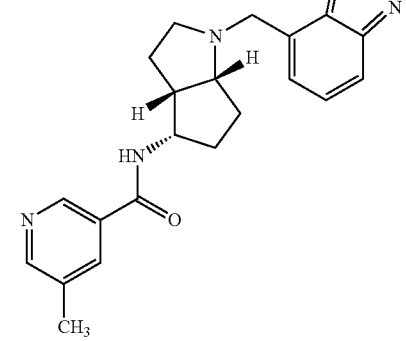 |

TABLE 1-continued
| EXAMPLE | COMPOUND |
|---|---|
| 52 | 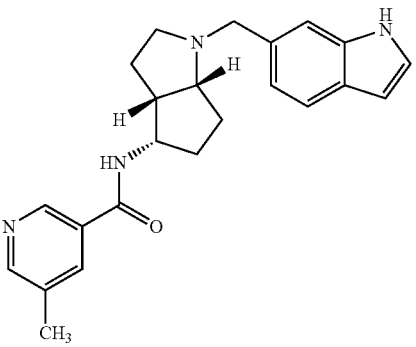 [SMILES: Cc1cncc(C(=O)N[C@H]2CC[C@@H]3[C@H]2CCN3Cc2ccc3cc[nH]c3c2)c1] |
| 53 | 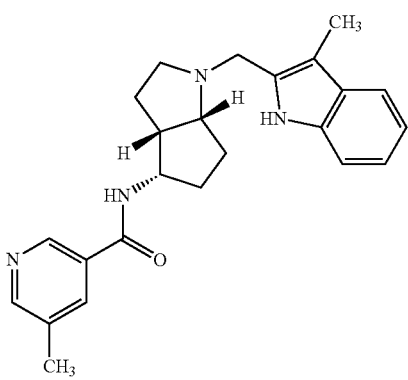 [SMILES: Cc1cncc(C(=O)N[C@H]2CC[C@@H]3[C@H]2CCN3Cc2[nH]c3ccccc3c2C)c1] |
| 54 | 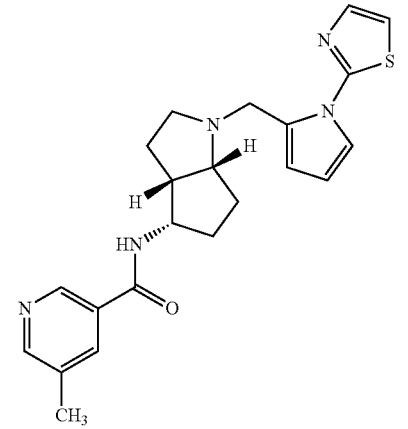 [SMILES: Cc1cncc(C(=O)N[C@H]2CC[C@@H]3[C@H]2CCN3Cc2cccn2-c2nccs2)c1] |
| 55 | 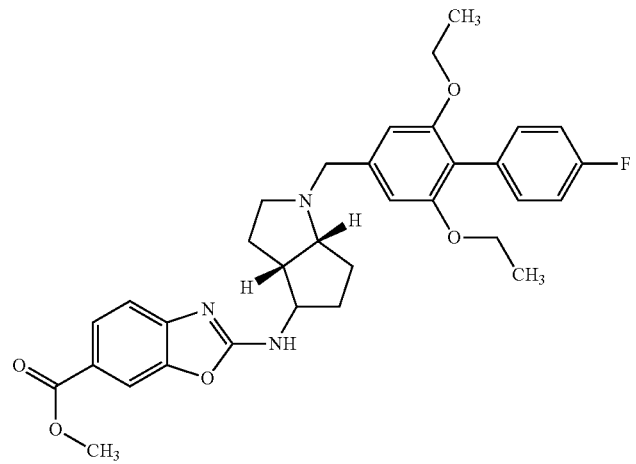 [SMILES: CCOc1cc(CN2CC[C@H]3C(Nc4nc5ccc(C(=O)OC)cc5o4)CC[C@H]32)cc(OCC)c1-c1ccc(F)cc1] |

TABLE 1-continued

| EXAMPLE | COMPOUND |
|---|---|
| 56 | |
| 57 | |
| 58 | |
| 59 | |
| 60 | |
| 61 | |
| 62 | |

TABLE 1-continued
| EXAMPLE | COMPOUND |
|---|---|
| 63 | 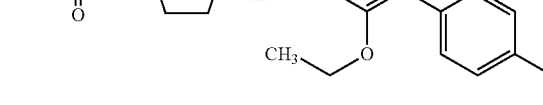 |
| 64 | 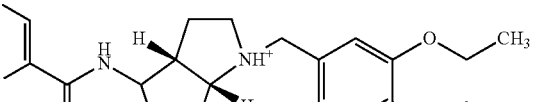 |
| 65 | 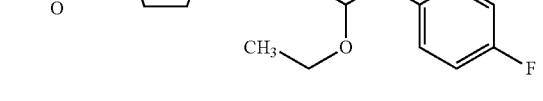 |
| 66 | 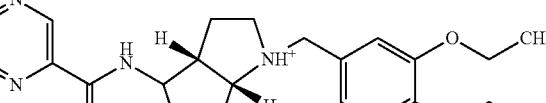 |
| 67 | 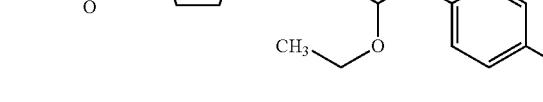 |
| 68 | 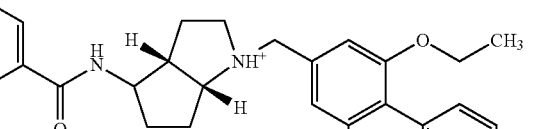 |
| 69 | 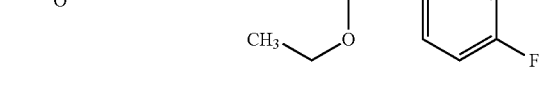 |

TABLE 1-continued

| EXAMPLE | COMPOUND |
|---|---|
| 70 | |
| 71 | |
| 72 | |
| 73 | |
| 74 | |
| 75 | |

TABLE 1-continued

| EXAMPLE | COMPOUND |
|---|---|
| 76 | |
| 77 | |
| 78 | |
| 79 | |
| 80 | |
| 81 | |
| 82 | |

TABLE 1-continued

| EXAMPLE | COMPOUND |
| --- | --- |
| 83 | |
| 84 | |
| 85 | |
| 86 | |
| 87 | |

TABLE 1-continued
| EXAMPLE | COMPOUND |
|---|---|
| 88 | 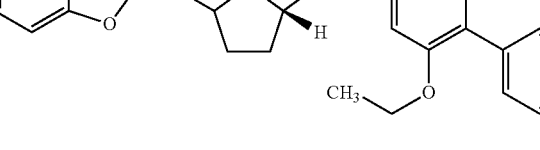 |
| 89 | 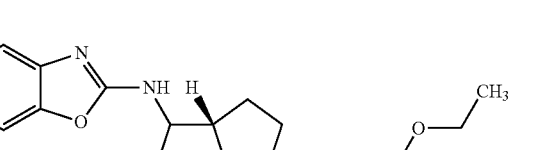 |
| 90 | 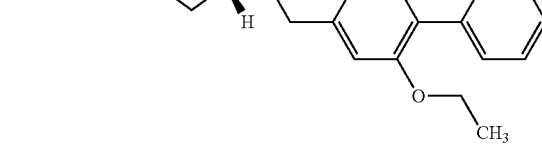 |
| 91 | 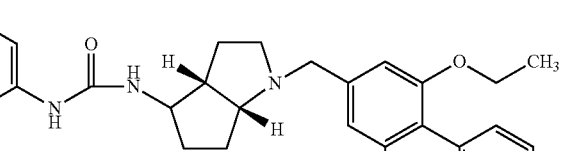 |
| 92 | 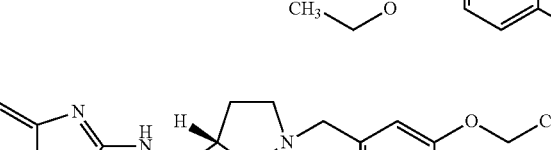 |
| 93 | 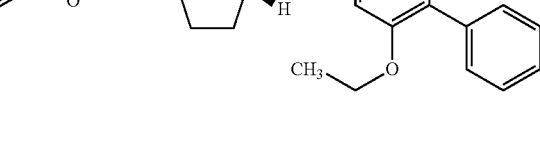 |

TABLE 1-continued

| EXAMPLE | COMPOUND |
|---|---|
| 94 | |
| 95 | |
| 96 | |
| 97 | |
| 98 | |
| 99 | |
| 100 | |

| EXAMPLE | COMPOUND |
|---------|----------|
| 101 |  |

In certain embodiments, the compounds described herein include:

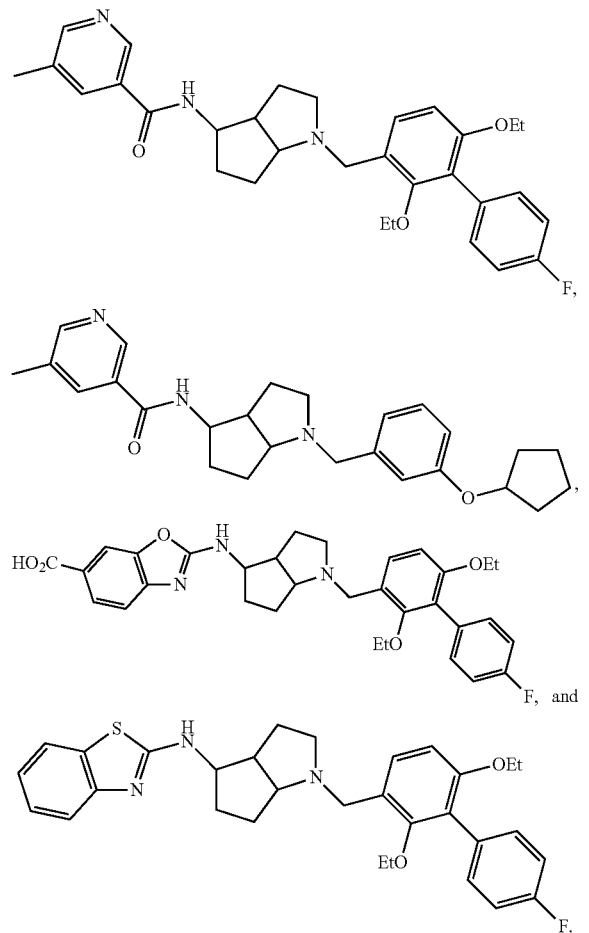

Definitions

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

The term "alkenyl" shall mean straight or branched-chain alkenes having the specified number of carbon atoms. Examples of alkenyl include vinyl, 1-propenyl, 1-butynyl, 2-butenyl, and the like.

The term "alkynyl" refers to straight or branched-chain alkynes having the specified number of carbon atoms. Examples of alkynyl include ethynyl, propynyl, butynyl, pentynyl, and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkyloxycarbonyl" refers to straight or branched chain esters of a carboxylic acid derivative of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aroyl" means the radical —OCR, where R is an aryl (benzoyl, napthoyl) group. Examples of aroyl groups include, but are not limited to:

"Aryl" means a mono- or polycyclic aromatic ring system containing carbon ring atoms. The preferred aryls are monocyclic or bicyclic 6-10 membered aromatic ring systems. Phenyl, and naphthyl are preferred aryls. The most preferred aryl is phenyl.

"Cycloalkyl" means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

"Heteroaroyl" means the radical —OCR, where R is a heteroaryl group. Examples of aroyl groups include, but are not limited to:

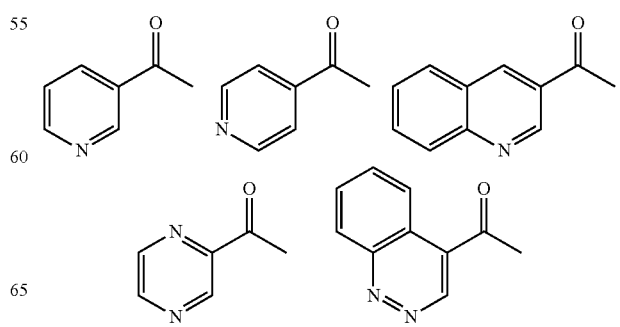

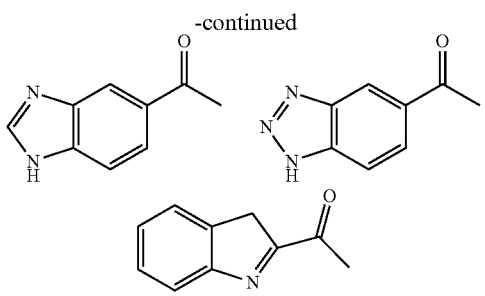

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

By "oxo" is meant the functional group "=O", such as, for example, (1) "C=(O)", that is a carbonyl group; (2) "S=(O)", that is, a sulfoxide group; and (3) "N=(O)", that is, an N-oxide group, such as pyridyl-N-oxide.

Compounds described herein may contain one or more asymmetric centers and can thus occur as racemates and racemic mixtures, single enantiomers, diastereomeric mixtures and individual diastereomers. The compounds described herein comprehend all such isomeric forms of the compounds described herein.

Compounds described herein may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound described herein may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds described herein.

It will be understood that, as used herein, references to the compounds described herein are meant to also include the pharmaceutically acceptable salts, and also salts that are not pharmaceutically acceptable when they are used as precursors to the free compounds or their pharmaceutically acceptable salts or in other synthetic manipulations.

The compounds described herein may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds described herein, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or pro-drug formulations.

Solvates, in particular hydrates, of the compounds described herein are included as well.

Methods of Making

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosphonium hexafluorophosphate, CAMP (cyclic adenosine-3′,5′-monophosphate), DAST ((diethylamino)sulfur trifluoride), DBU (1,8-diazabicyclo[5.4.0]undec-7-ene), DCM (dichloromethane), DIBAL (diisobutylaluminum hydride), DIEA (diisopropylethyl amine), DMAP (4-(dimethylamino)pyridine), DMF (N,N-dimethylformamide), DPPF (1,1′-bis-diphenylphosphino ferrocene), EDC (1-(3-dimethylaminopropyl)-3-ethylcarbodiimide hydrochloride), Et$_3$N (triethylamine), GST (glutathione transferase), HOBt (1-hydroxybenzotriazole), LAH (lithium aluminum hydride), Ms (methanesulfonyl; mesyl; or SO$_2$Me), MsO (methanesulfonate or mesylate), MCPBA (meta-chloro perbenzoic acid), NaHMDS (sodium hexamethyldisilazane), NBS (N-bromosuccinimide), NCS (N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or SO$_2$NH$_2$), SPA (scintillation proximity assay), Th (2- or 3-thienyl), TFA (trifluoroacetic acid), THF (Tetrahydrofuran), Thi (Thiophenediyl), TLC (thin layer chromatography), TMEDA (N,N,N′,N′-tetramethylethylenediamine), TMSI (trimethylsilyl iodide), Tr or trityl(N-triphenylmethyl), C$_3$H$_5$ (Allyl), Me (methyl), Et (ethyl), EtOAc (ethyl acetate), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the general Schemes provided below as well as the procedures provided in the Examples. The following Schemes and Examples further describe, but do not limit, the scope.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Also described herein are methods of making the compounds described above.

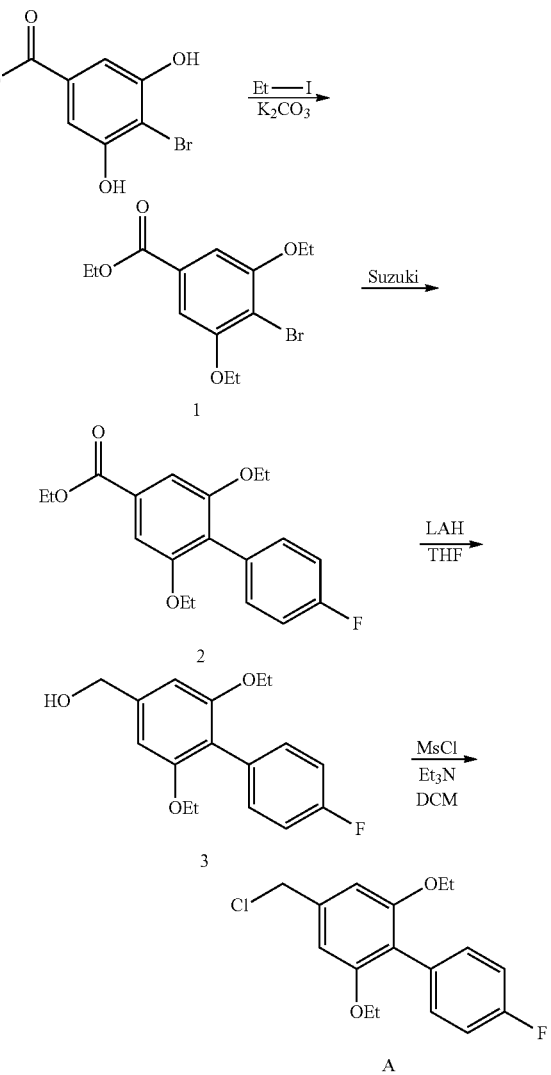

Ethyl 4-bromo-3,5-diethoxybenzoate (Compound 1)

(Compound 1)

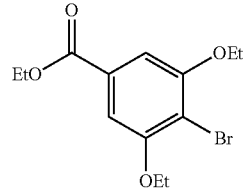

Ethyl 4-bromo-3,5-diethoxybenzoate

Iodoethane (17.3 mL, 215 mmol) was added to a stirred mixture of 4-bromo-3,5-dihydroxybenzoic acid (10 g, 42.9 mmol) and potassium carbonate (26.7 g, 193 mmol) in DMF (100 mL) and the mixture was stirred at room temperature for 18 h, and then was partitioned between EtOAc and water. The aqueous phase was extracted with EtOAc. The combined organic phases were washed with water (2×), brine, dried (MgSO₄) and concentrated to give Compound 1. H NMR (500 MHz, CDCl3, ppm): 1.4 (t, 3H), 1.5 (t, 6H), 4.2 (q, 4H), 4.4 (q, 2H), 7.2 (s, 2H).

Ethyl 2,6-diethoxy-4'-fluorobiphenyl-4-carboxylate
(Compound 2)

(Compound 2)

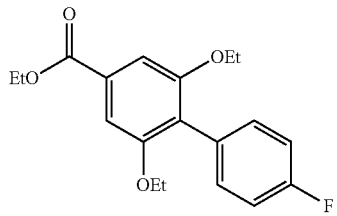

Ethyl 2,6-diethoxy-4'-fluorobiphenyl-4-carboxylate

Dioxane (120 mL) was added to a degassed mix of tri-t-butylphosphonium tetrafluoroborate (0.73 g, 2.5 mmol), 4-fluorophenylboronic acid (11.8 g, 84 mmol), Tris(dibenzylideneacetone)dipalladium(0) (0.77 g, 0.84 mmol), CsF (23.7 g, 156 mmol) and Compound 1 (13.4 g, 42 mmol). The mixture was stirred at 90° C. under nitrogen for 20 h, and then was partitioned between EtOAc and water. The aqueous phase was filtered and extracted with EtOAc. The combined organic phases were washed with water, brine, dried (MgSO₄), and concentrated. The residue was chromatographed on silica gel columns, eluting with EtOAc/Hexane. Product fractions were combined and concentrated to give Compound 2. LC-MS, M+1=333.1; H NMR (500 MHz, CDCl3, ppm): 1.3 (t, 6H), 1.45 (t, 3H), 4.1 (q, 4H), 4.4 (q, 2H), 7.1 (m, 2H), 7.2 (s, 2H), 7.4 (m, 2H).

(2,6-Diethoxy-4'-fluorobiphenyl-4yl)methanol
(Compound 3)

(Compound 3)

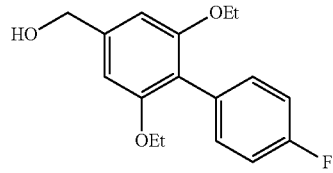

(2,6-Diethoxy-4'-fluorobiphenyl-4-yl)methanol

A solution of lithium aluminumhydride (34 ml, 34 mmol) in THF was added dropwise over 30 min to a stirred solution of Compound 2 (14 g, 42 mmol) in THF (120 mL) at room temperature. After 2 h, TLC showed no starting material left. The reaction mixture was stored in the fridge overnight and was quenched by the sequential addition of water (4 mL), aq NaOH (0.5 M, 4 mL) and water (4 mL). The mixture was filtered through CELITE (diatomaceous earth), washed thoroughly with EtOAc and the filtrate was concentrated to give Compound 3 as white solid. H NMR (500 MHz, CDCl3, ppm): 1.3 (t, 6H), 1.8 (t, 1H), 4.0 (q, 4H), 4.7 (d, 2H), 6.7 (s, 2H), 7.1 (m, 2H), 7.4 (m, 2H).

4-(Chloromethyl)-2,6-diethoxy-4'-fluorobiphenyl
(Intermediate A)

(Intermediate A)

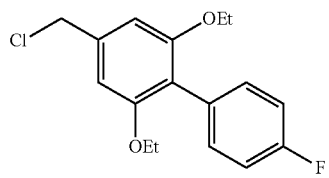

4-(Chloromethyl)-2,6-diethoxy-4'-fluorobiphenyl

Methanesulfonyl chloride (1.6 mL, 20.7 mmol) was added dropwise to a stirred solution of Compound 3 (5 g, 17.2 mmol) and triethylamine (3.6 mL, 25.8 mmol) in dichloromethane (40 mL) and the mixture was stirred at room temperature for 18 h. The mixture was partitioned between EtOAc and water. The aqueous phase was extracted with EtOAc. The combined organic phases were washed with water, brine, dried (MgSO₄) and concentrated. The residue was chromatographed on a silica gel column, eluting with EtOAc/Hexane. Product fractions were combined and concentrated to give intermediate A. H NMR (500 MHz, CDCl3, ppm): 1.3 (t, 6H), 4.0 (q, 4H), 4.6 (s, 2H), 6.7 (s, 2H), 7.1 (m, 2H), 7.4 (m, 2H). LC-MS, m+1=309.1

Scheme 2. Synthesis of Intermediate B

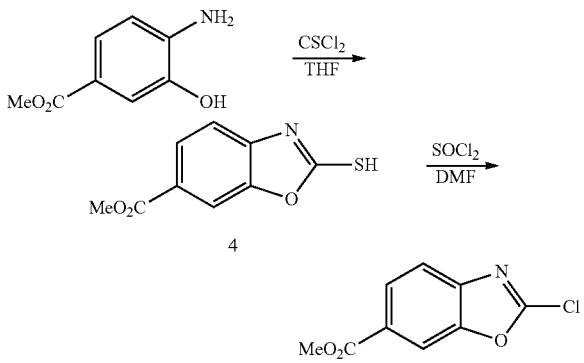

Methyl 2-mercapto-1,3-benzoxazole-6-carboxylate
(Compound 4)

(Compound 4)

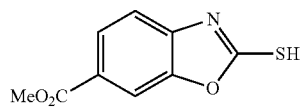

Methyl 2-mercapto-1,3-benzoxazole-6-carboxylate

To a stirred solution of methyl 4-amino-3-hydroxybenzoate (4.45 g, 26.6 mmol) in THF (250 ml) at room temperature, thiophosgene (2.4 mL, 32 mmol) was added slowly via a syringe pump over a period of 1 hr. After stirring for 4 hr, excess thiophosgene was quenched by addition of a saturated aqueous solution of NH₄Cl (100 mL), and the THF was removed by evaporation under reduced pressure. More water was added, and the aqueous mixture was extracted with EtOAc (3×). The Combined organic phase was washed with brine, dried (MgSO₄), concentrated in vacuo to give Compound 4 as a tan solid. LC-MS, M+1=210

Methyl 2chloro-1,3benzoxazole-6-carboxylate
(Intermediate B)

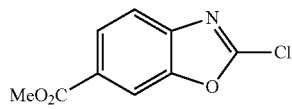

To Compound 4 (2 g, 9.5 mmol), SOCl$_2$ (9.8 ml, 134 mmol) and DMF (0.8 mL, 10 mmol) was added at room temperature. The reaction mixture heated to reflux for 15 min. The solvent was removed under reduced pressure. The crude oil was azeotroped with xylene twice.

The residue was dissolved in a minimum amount of DCM/MeOH, and then loaded onto a silica gel column, eluting with EtOAc/isohexane to give intermediate B as a white solid. H NMR (500 MHz, CDCl3, ppm): 4.0 (s, 3H), 7.8 (d, 1H), 8.1 (d, 1H), 8.3 (s, 1H). LC-MS, M+1=212.1

Scheme 3. Synthesis of Example 1

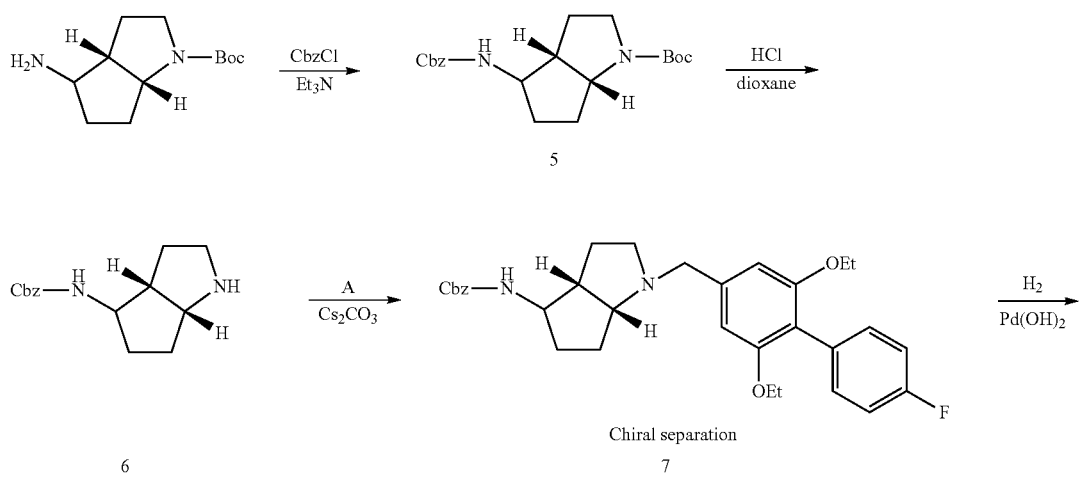

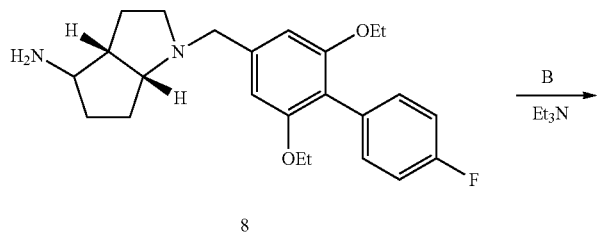

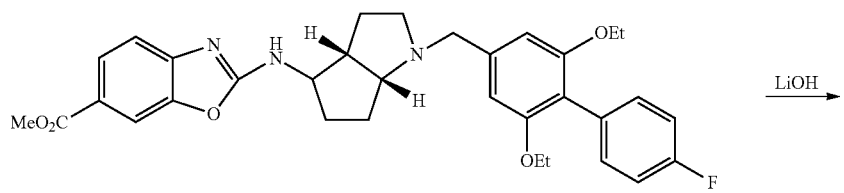

Example 55

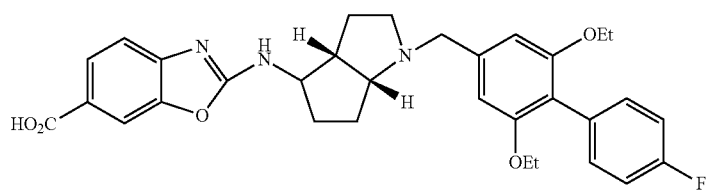

Example 1 tert-Butyl 4-{[(benzyloxy)carbonyl]
amino}hexhydrocyclopenta[b]pyrrole-1(2H)-carboxylate (Compound 5, cis, Racemic)

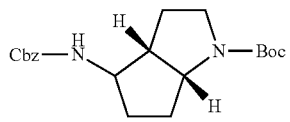 [SMILES: CC(C)(C)OC(=O)N1CC[C@H]2C(NC(=O)OCc3ccccc3)CC[C@H]21]

Benzyl chloroformate (1.76 mL, 12.3 mmol) was added dropwise to a stirred and cooled (0° C.) mixture of tert-butyl 4-aminohexahydrocyclopenta[b]pyrrole-1(2H)-carboxylate (cis-isomer, racemic, >95% of one diastereomer, 1.4 g, 6.2 mmol) and triethylamine (3.5 mL, 24.7 mmol) in dichloromethane, and the resulting mixture was stirred at room temperature overnight. The reaction mixture was diluted with dichloromethane and washed with saturated aqueous NaHCO$_3$, water and brine. The mixture was dried (MgSO$_4$), filtered and the solvent was evaporated under reduced pressure. The residue was purified by column chromatography on silica gel, eluting with EtOAc/isohexane to give Compound 5 as colorless oil. LC-MS, M+1-Boc=261.3

Benzyloctahydrocyclopenta[b]pyrrol-4-ylcarbamate (Compound 6, cis, Racemic)

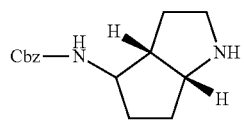 [SMILES: O=C(NC1CC[C@H]2NCC[C@@H]12)OCc1ccccc1]

To a solution of Compound 5 (1.18 g, 3.3 mmol) in 8 mL of dioxane, HCl in dioxane (4M, 16 ml, 64 mmol) was added at room temperature. After 2 hour, LC-MS showed no starting material, and product peak presented. The solvent was removed under reduced pressure, and then the product material was dried using high vacuum to give Compound 6. LC-MS, m+1=261.3

Benzyl {1-[(2,6-diethoxy-4'-fluorobiphenyl-4-yl)methyl]octahydrocyclopenta[b]pyrrol-4-yl}carbamate (Compound 7, cis,)

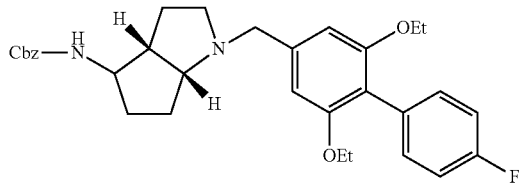 [SMILES: CCOc1cc(CN2CC[C@H]3C(NC(=O)OCc4ccccc4)CC[C@H]32)cc(OCC)c1-c1ccc(F)cc1]

The reactants, Intermediate A (379 mg, 1.2 mmol), Compound 6 (364 mg, 1.2 mmol), and cesium carbonate (1.2 g, 3.3 mmol) were mixed in 10 mL of DMF and stirred at room temperature overnight. The resulting mixture was diluted with EtOAc, washed with saturated aqueous NaHCO$_3$, dried (MgSO$_4$), filtered and the solvent was evaporated under reduced pressure. The residue was purified by column chromatography on silica gel, eluting with EtOAc/Hexanes to give racemic Compound 7 as a colorless oil. LC-MS, M+1=533.5. The minor diastereomer (~2%) was separated at this step. The racemic compounds were separated with a Chiral OD column (5% iPrOH/Heptane. 9 ml/min flow rate) to obtain the first Enantiomer A of Compound 7 and second Enantiomer B of Compound 7.

1-[(2,6-Diethoxy-4'-fluorobiphenyl-4-yl)methyl]octahydrocyclopenta[b]pyrrol-4-amine (Compound 8, single enantiomer)

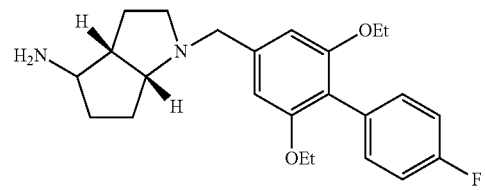 [SMILES: CCOc1cc(CN2CC[C@H]3C(N)CC[C@H]32)cc(OCC)c1-c1ccc(F)cc1]

To a solution of Enantiomer A of Compound 7 (137 mg, 0.25 mmol) in MeOH (2.5 mL) Pd(OH)$_2$ on carbon (50% wt, 29 mg, 0.1 mmol) was added at room temperature. The reaction vessel was purged with nitrogen three times. Then the reaction mixture was stirred under a hydrogen balloon for 1 h. The reaction mixture was filtered through CELITE (diatomaceous earth) and concentrated to give Compound 8 as a colorless gum. LC-MS, M+1=399.2

Methyl 2-({1-[(2,6-diethoxy-4'-fluorobiphenyl-4-yl)methyl]octahydrocyclopenta[b]pyrrol-4-yl}amino)-1,3-benzoxazole-6-carboxylate (Example 55, single enantiomer)

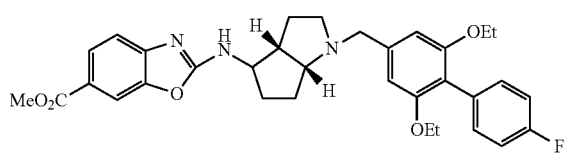 [SMILES: CCOc1cc(CN2CC[C@H]3C(Nc4nc5ccc(C(=O)OC)cc5o4)CC[C@H]32)cc(OCC)c1-c1ccc(F)cc1]

To a solution of Compound 8 (98 mg, 0.25 mmol) in acetonitrile (1.5 mL) Intermediate B (62.4 mg, 0.3 mmol) and triethylamine (0.07 ml, 0.5 mmol) was added. The reaction mixture was heated in a sealed tube at 80° C. for 1 h. The solvent was removed under reduced pressure, and the residue was purified by preparative thin layer chromatograph (5% MeOH/DCM) to give Compound 9 as a white foam. LC-MS, M+1=574.3

2-({1-[(2,6-Diethoxy-4'-fluorobiphenyl-4-yl)methyl]octahydrocyclopenta[b]pyrrol-4-yl}amino)-1,3-benzoxazole-6-carboxylic acid (Example 1, single enantiomer)

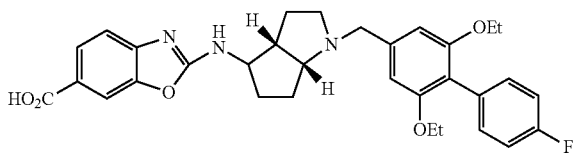 [SMILES: CCOc1cc(CN2CC[C@H]3C(Nc4nc5ccc(C(=O)O)cc5o4)CC[C@H]32)cc(OCC)c1-c1ccc(F)cc1]

To a stirred solution of Compound 9 (95 mg, 0.17 mmol) in THF/MeOH/H$_2$O (1/0.5/0.5 mL) lithium hydroxide monohydrate (104 mg, 2.5 mmol) was added. The reaction mixture was warmed up to 50° C. for 2.5 h. The reaction mixture was acidified with 50% formic acid/CH$_3$CN, and then purified by reverse phase HPLC (C18) followed by lyophilization to give Example 1 as white solid. H NMR (400 MHz, CDCl3, ppm): 1.2 (t, 6H), 1.6 (m, 1H), 2.0 (m, 3H), 2.2 (m, 2H), 3.0 (m, 1H), 3.2 (m, 1H), 3.6 (m, 1H), 3.8 (m, 1H), 4.0 (m, 5H), 4.5 (m, 1H), 4.8 (m, 1H), 7.0 (s, 2H), 7.1 (m, 2H), 7.4 (m, 3H), 7.7 (broad, 1H), 8.0 (m, 1H), 8.8 (s, 1H). LC-MS, M+1=560.44

Scheme 4. Synthesis of Example 2

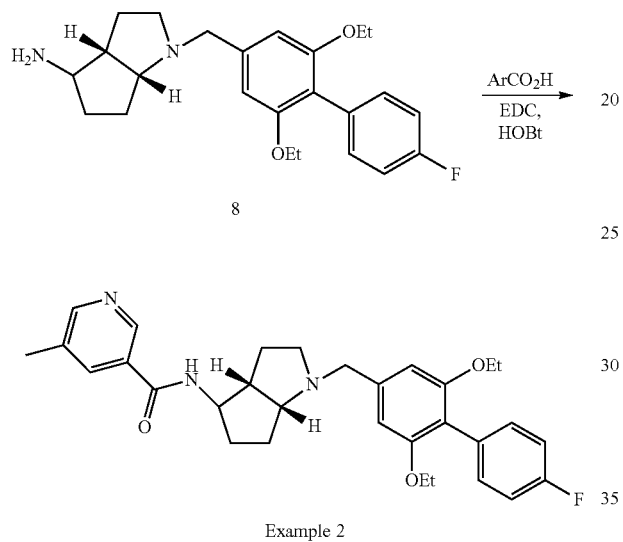

N-{1-[(2,6-Diethoxy-4'-fluorobiphenyl-4-yl)methyl]octahydrocyclopenta[b]pyrrol-4-yl}-2-methylisonicotinamide (Example 2)

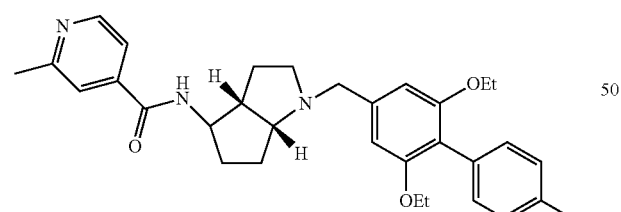

Compound 8 (40 mg, 0.1 mmol), EDC (0.15 mmol), HOBT (0.15 mmol), triethylamine (0.2 mmol), and 5-methyl 3-pyridine carboxylic acid (0.12 mmol) were stirred in acetonitrile (1 mL) at room temperature overnight. The product was purified by mass-directed column chromatography. LC-MS, M+1=518.3

Table 2 shows other compounds that can be made by a similar process using the appropriate substitutions.

TABLE 2

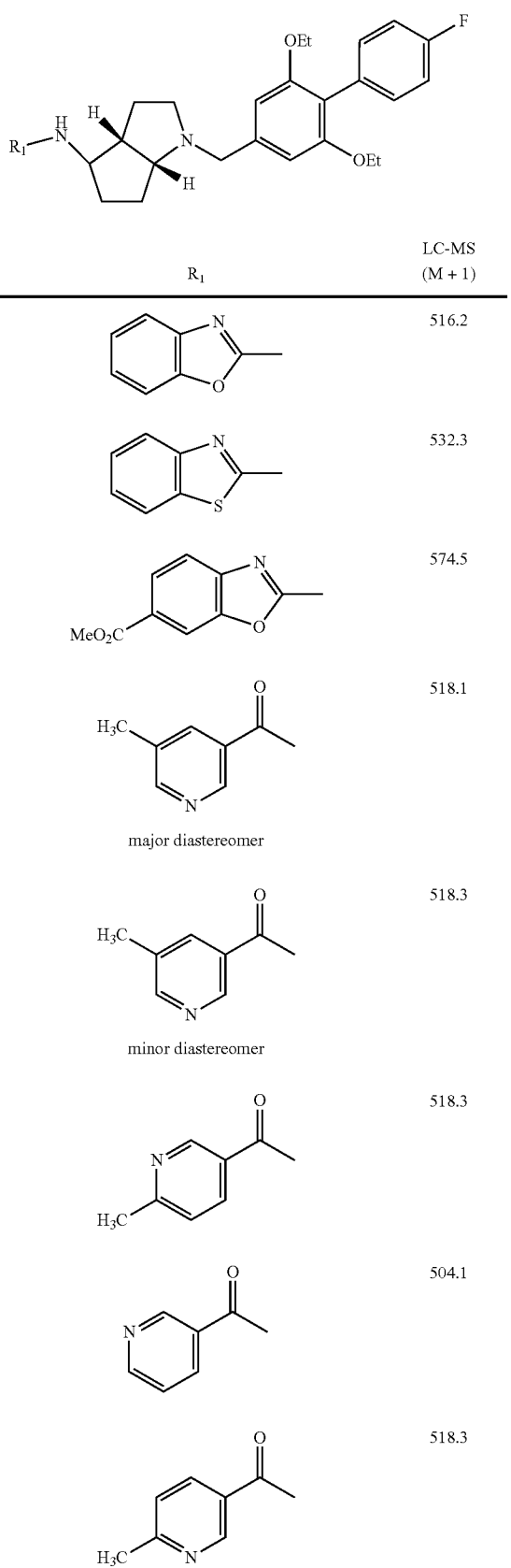

TABLE 2-continued
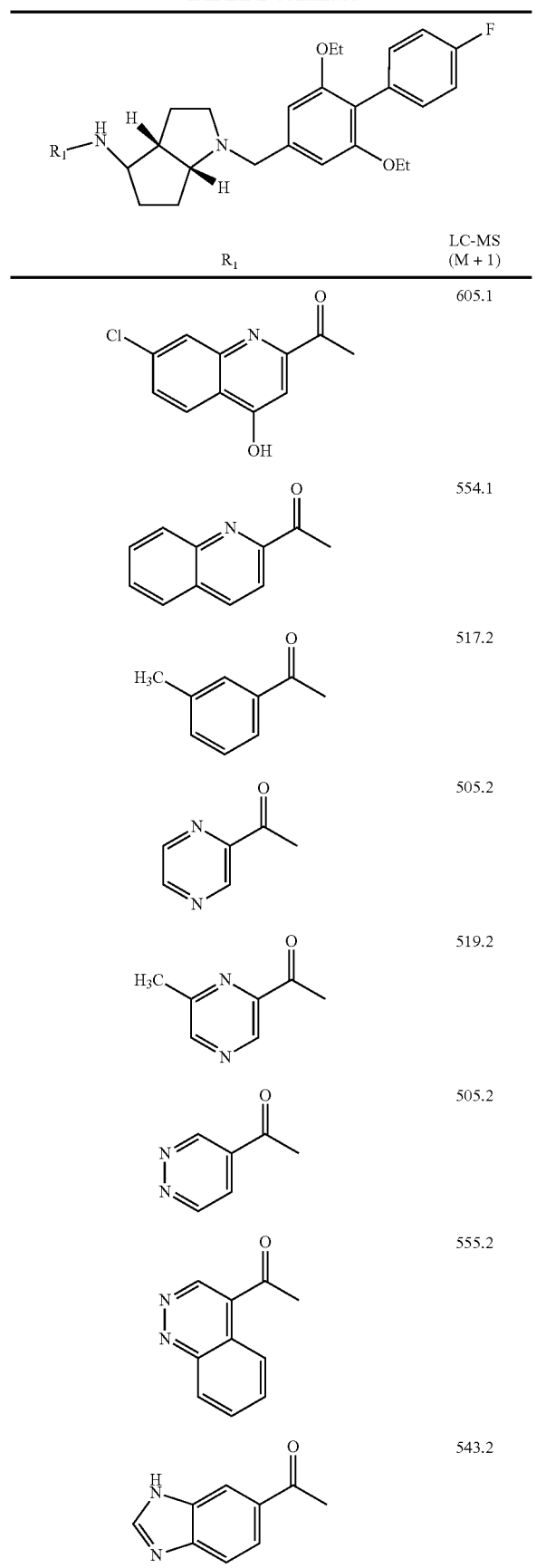
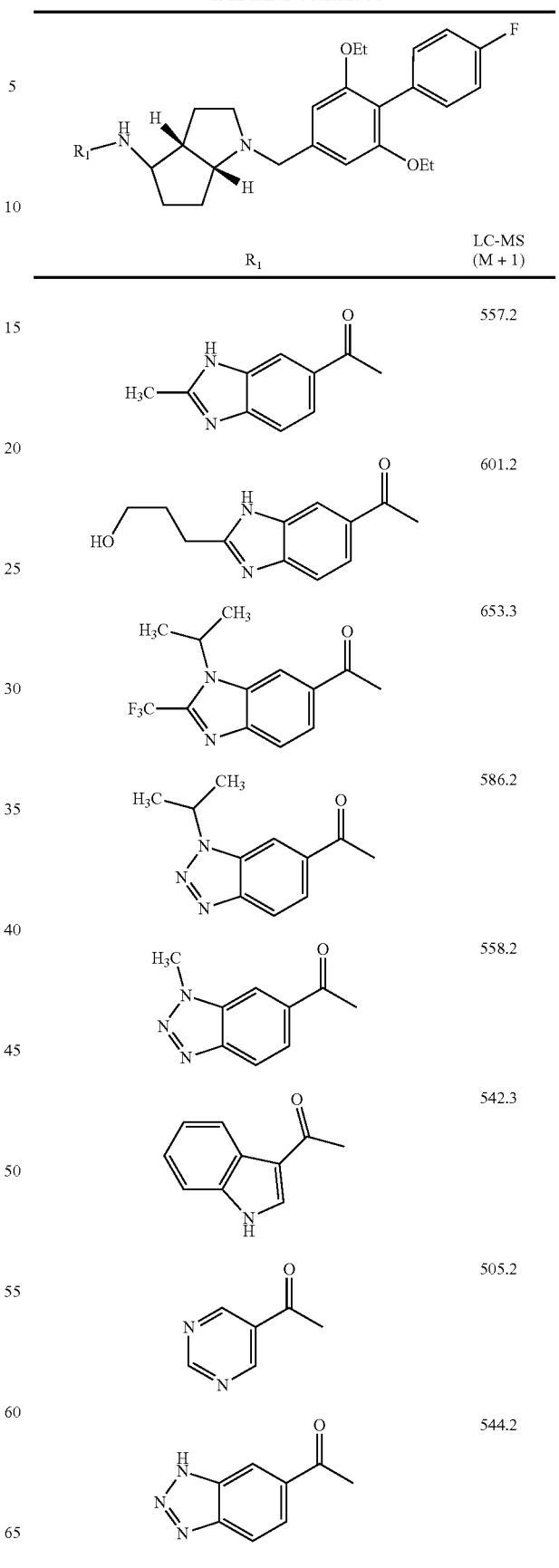

TABLE 2-continued

[Structure: Bicyclic pyrrolidine core with R₁-NH- substituent and N-CH₂-(2,6-diethoxy-4'-fluorobiphenyl) substituent]

| R₁ | LC-MS (M + 1) |
|---|---|
| 2-methylbenzoxazol-6-yl with MeO₂C at 5-position, Enantiomer A | 574.5 |
| 2-methylbenzoxazol-6-yl with MeO₂C at 5-position, Enantiomer B | 574.5 |
| 2-methylbenzoxazol-6-yl with HO₂C at 5-position, Enantiomer A | 560.4 |
| 2-methylbenzoxazol-6-yl with HO₂C at 5-position, Enantiomer B | 560.4 |
| 3-methylphenyl acetyl, Enantiomer A | 517.3 |
| 3-methylphenyl acetyl, Enantiomer B | 517.3 |
| 6-fluoro-2-methylbenzoxazol-5-yl | 534.3 |
| 6-trifluoromethoxy-2-methylbenzoxazol-5-yl | 660.3 |
| 6-chloro-2-methylbenzoxazol-5-yl | 550.3 |
| 5-(MeO₂C)-2-methylbenzoxazol-6-yl | 574.5 |
| 5-(HO₂C)-2-methylbenzoxazol-6-yl | 560.4 |
| 5-(ethylsulfonyl)-2-methylbenzoxazol-6-yl | 608.3 |
| 5-nitro-2-methylbenzoxazol-6-yl | 561.3 |
| 3-methylphenyl acetamide | 532.5 |
| 5-amino-2-methylbenzoxazol-6-yl | 531.5 |
| 5-(MeO₂CCH₂)-2-methylbenzoxazol-6-yl | 588.7 |
| 5-(methylsulfonamido)-2-methylbenzoxazol-6-yl | 609.6 |
| 5-(HO₂CCH₂)-2-methylbenzoxazol-6-yl | 574.5 |
| benzyl acetate | 533.5 |

TABLE 2-continued

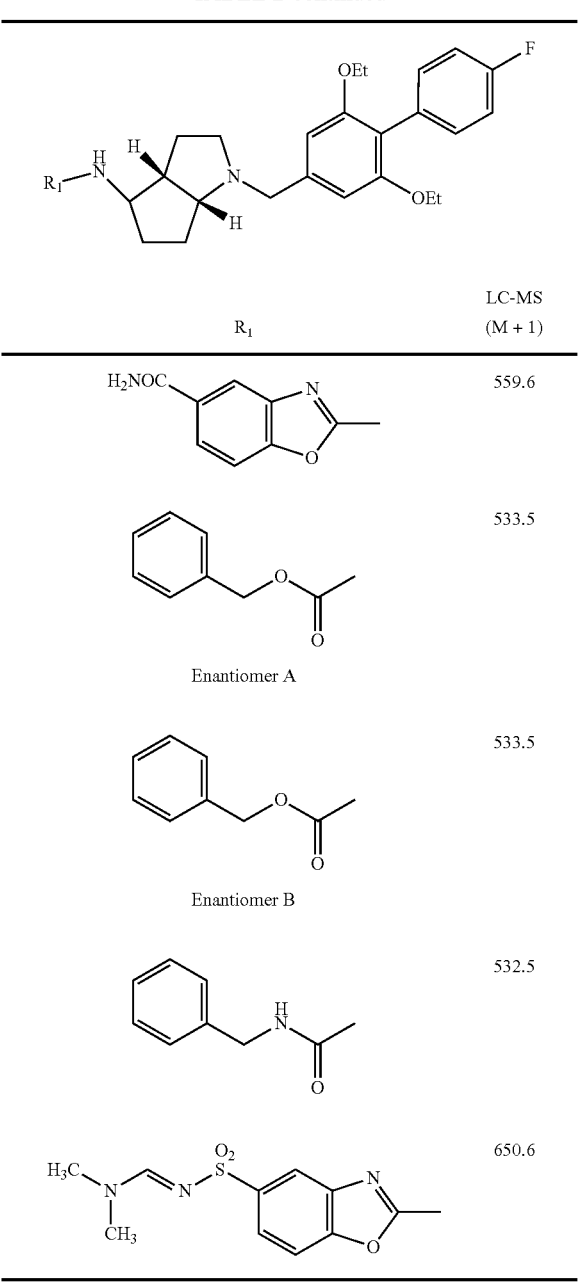

| $R_1$ | LC-MS (M + 1) |
|---|---|
| H₂NOC-(2-methylbenzoxazol-5-yl) | 559.6 |
| benzyl acetate (Enantiomer A) | 533.5 |
| benzyl acetate (Enantiomer B) | 533.5 |
| N-benzyl acetamide | 532.5 |
| H₃C-N(CH₃)-CH=N-SO₂-(2-methylbenzoxazol-5-yl) | 650.6 |

Scheme 5. Synthesis of Example 5

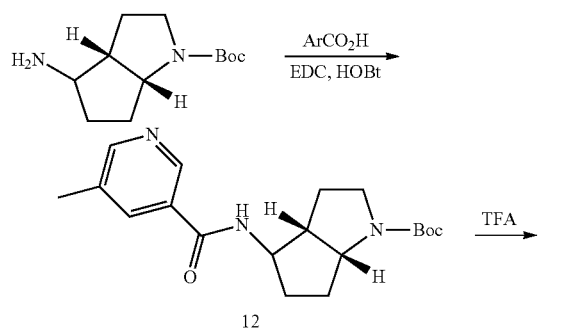

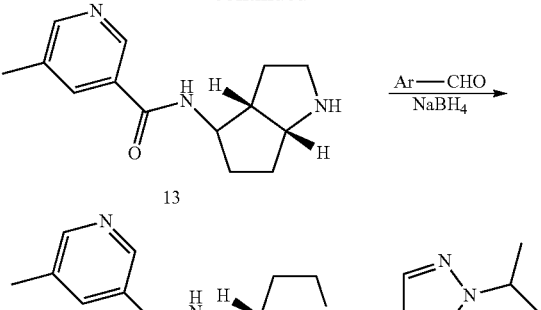

tert-Butyl 4-{[(5-methylpyridin-3yl)carbonyl]amino}hexahydrocyclopenta[b]pyrrole-1(2H)-carboxylate (Compound 12)

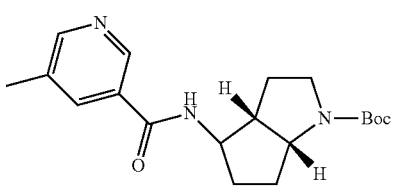 [SMILES: Cc1cncc(C(=O)NC2CC[C@@H]3[C@H]2CCN3C(=O)OC(C)(C)C)c1]

A 100 mL round bottom flask was charged with a magnetic stirbar, EDC (3.8 g, 19.9 mmol), HOBT (4.1 g, 26.5 mmol), 5-methyl, 3-pyridine carboxylic acid (2.2 g, 15.9 mmol) and methylenechloride (35 mL). tert-Butyl 4-(aminomethyl)hexahydrocyclopenta[b]pyrrole-1(2H)-carboxylate (cis-isomer, racemic, >95% of one diastereomer, 3 g, 13.3 mmol) was added over 10 minutes and the reaction mixture was allowed to stir for 9 h at room temperature. The solvent was removed in vacuo, and the product was dissolved in chloroform and washed with water. The organic layer was dried with magnesium sulfate and solvent was removed in vacuo. The final compound was purified using reverse-phase HPLC to afford Compound 12. LC-MS, M+1=346.0

5-Methyl-N-(octahydrocyclopenta[b]pyrrol-4-yl)nicotinamide (Compound 13)

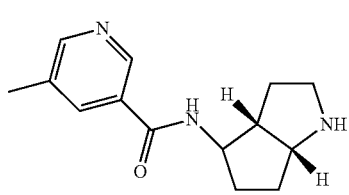 [SMILES: Cc1cncc(C(=O)NC2CC[C@H]3NCC[C@@H]23)c1]

A 50 mL round bottom flask was charged with a magnetic stirbar, Compound 12 (1.5 g, 6.11 mmol) and dichloromethane (25 mL). Trifluoroacetic acid (2.1 g, 18.3 mmol) was added and the reaction mixture was allowed to stir at room temperature for 4 hours. Solvent and volatiles were removed in vacuo overnight to yield Compound 13 as its TFA salt.

N-[1-(1-isopropyl-1H-pyrazol-4-yl)octahydrocyclopenta[b]pyrrol-4-yl]-5-methylnicotinamide (Example 5)

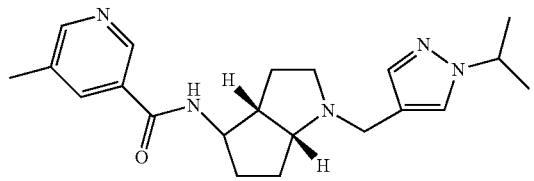 [SMILES: Cc1cncc(C(=O)NC2CC[C@@H]3[C@H]2CCN3Cc2cnn(C(C)C)c2)c1]

A 5 mL vial was charged with a magnetic stirbar, the aromatic aldehyde (0.1 mmol), dimethylformamide (1.5 mL) and triethylamine (0.3 mmol). The mixture was allowed to stir for 10 min at room temperature. Acetic acid (0.75 mmol) and sodium borohydride (0.15 mmol) were then added and allowed to stir for 5 min prior to addition of Compound 13 (0.1 mmol). The product was purified by mass-directed column chromatography. LC-MS, M+1=368.3

Table 3 shows other compounds that can be made by a similar process using appropriate substitutions.

TABLE 3-continued
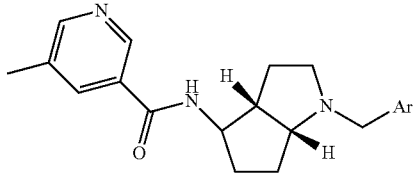
| —Ar | LC-MS (M + 1) |
|---|---|
| 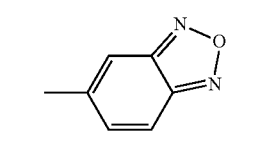 | 378.2 |
| 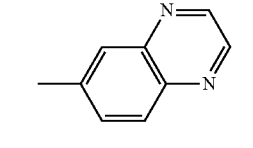 | 388.2 |
| 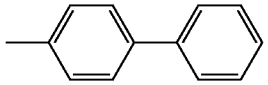 | 412.3 |
| 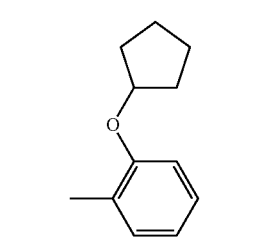 | 420.3 |
| 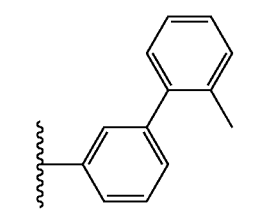 [SMILES: *c1cccc(-c2ccccc2C)c1] | 426.3 |
| 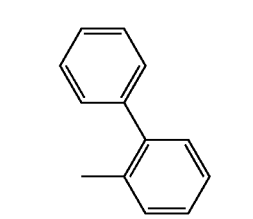 | 412.3 |
| 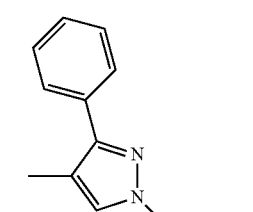 | 478.3 |
TABLE 3-continued
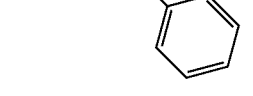
| —Ar | LC-MS (M + 1) |
|---|---|
| 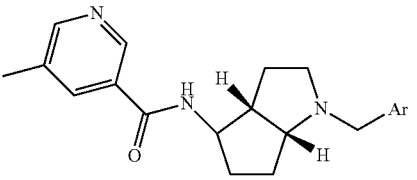 | 420.3 |
| 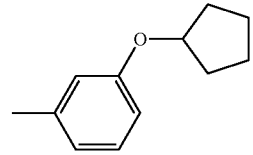 | 426.3 |
| 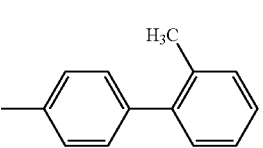 | 412.3 |
|  | 403.3 |
| 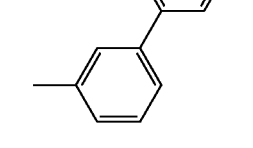 | 394.2 |
| 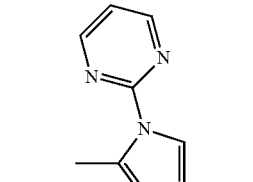 | 420.3 |
| 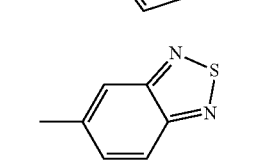 | 436.2 |

TABLE 3-continued
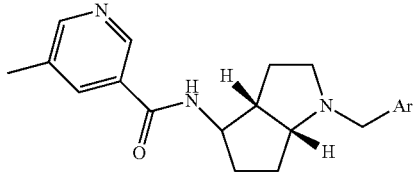
| —Ar | LC-MS (M + 1) |
|---|---|
| 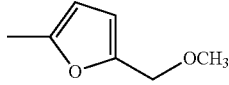 | 370.3 |
| 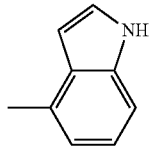 | 375.3 |
| 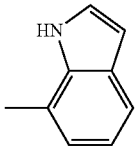 | 375.2 |
| 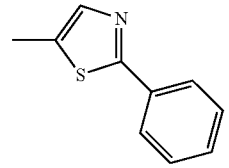 | 419.2 |
| 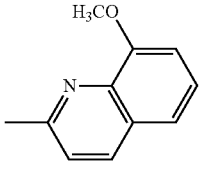 | 417.3 |
| 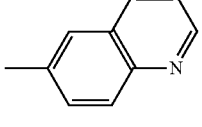 | 387.2 |
| 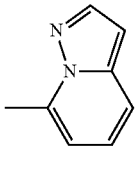 | 376.3 |
| 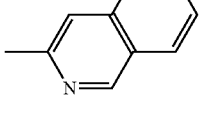 | 387.3 |
TABLE 3-continued
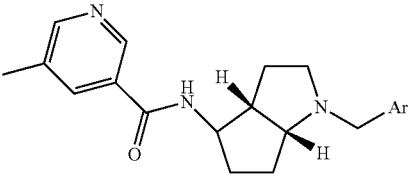
| —Ar | LC-MS (M + 1) |
|---|---|
| 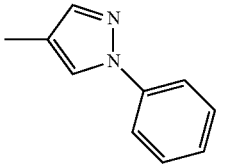 | 402.3 |
| 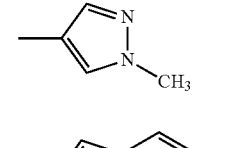 | 340.3 |
| 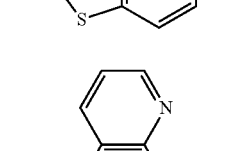 | 392.2 |
| 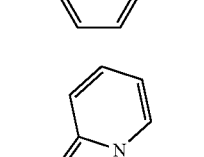 | 387.2 |
| 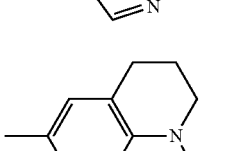 | 376.2 |
| 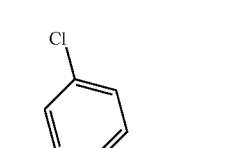 | 405.3 |
| 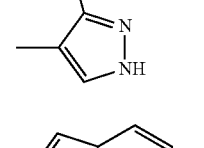 | 436.6 |
| 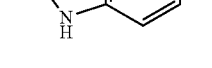 | 375.2 |

TABLE 3-continued

| —Ar | LC-MS (M + 1) |
|---|---|
| 3-phenyl-1H-pyrazol-5-yl (methyl substituted) | 402.3 |
| benzothiazol-2-yl (methyl substituted) | 393.2 |
| benzimidazol-2-yl (methyl substituted) | 376.2 |
| 4-(2-oxopyrrolidin-1-yl)phenyl (methyl substituted) | 419.2 |
| benzo[c][1,2,5]oxadiazol-4-yl (methyl substituted) | 378.2 |
| 1H-indol-6-yl (methyl substituted) | 375.2 |
| 3-methyl-1H-indol-2-yl | 389.3 |
| 2-(thiazol-2-yl)-1H-pyrrol-5-yl (methyl substituted) | 408.2 |

Methods of Treatment

Also described herein are methods for the treatment, control, or prevention of diseases that are responsive to antagonism of SSTR5. The compounds described herein are potent and selective antagonists of the SSTR5. The compounds are efficacious in the treatment of diseases that are modulated by SSTR5 ligands, which are generally antagonists. Such diseases include, but are not limited to diabetes, hyperglycemia, insulin resistance, obesity, lipid disorders, atherosclerosis, and metabolic syndrome.

Therefore, described herein, are methods for the treatment, control, or prevention of diabetes, hyperglycemia, insulin resistance, obesity, lipid disorders, atherosclerosis, and metabolic syndrome by administering, to a mammal, the compounds and pharmaceutical compositions described herein.

The term "diabetes" as used herein includes both insulin-dependent diabetes (that is, also known as IDDM, type-1 diabetes), and insulin-independent diabetes (that is, also known as NIDDM, type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

The compounds and compositions described herein are useful for treatment of both type 1 diabetes and type 2 diabetes. The compounds and compositions are especially useful for treatment of type 2 diabetes. The compounds and compositions described herein are especially useful for treatment and/or prevention of pre-diabetes. Also, the compounds and compositions described herein are especially useful for treatment and/or prevention of gestational diabetes mellitus.

Treatment of diabetes mellitus refers to the administration of a compound or combination described herein to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes. Yet another outcome of treatment is to increase hepatic insulin sensitivity.

Prevention of diabetes mellitus, in particular diabetes associated with obesity, refers to the administration of a compound or combination described herein to prevent or treat the onset of diabetes in a subject in need thereof. A subject in need of preventing diabetes is a prediabetic subject. In certain embodiments the compounds described herein can be useful in the treatment, control or prevention of type 2 diabetes and in the treatment, control and prevention of the numerous conditions that often accompany type 2 diabetes, including metabolic Syndrome X, reactive hypoglycemia, and diabetic dyslipidemia. Obesity, discussed below, is another condition that is often found with type 2 diabetes that may respond to treatment with the compounds described herein.

The following diseases, disorders and conditions are related to type 2 diabetes, and therefore may be treated, controlled or in some cases prevented, by treatment with the compounds described herein: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "metabolic syndrome", also known as Syndrome X, is defined in the Third Report of the National Cholesterol Education Program Expert Panel on Detection, Evaluation and Treatment of High Blood Cholesterol in Adults (ATP-III). B. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations described herein to reduce or maintain the body weight of an obese subject. One outcome of treatment may be reducing the body weight of an obese subject relative to that subject's body weight immediately before the administration of the compounds or combinations described herein. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations described herein to reduce or maintain the body weight of a subject at risk of obesity. One outcome of prevention may be reducing the body weight of a subject at risk of obesity relative to that subject's body weight immediately before the administration of the compounds or combinations described herein. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, type 2 diabetes, polycystic ovary disease, cardiovascular diseases, osteoarthritis, dermatological disorders, hypertension, insulin resistance, hypercholesterolemia, hypertriglyceridemia, and cholelithiasis.

In certain embodiments, the pharmaceutical formulations described herein are useful for the treatment, control, or prevention of obesity and the conditions associated with obesity. Obesity may be due to any cause, whether genetic or environmental. Other conditions associated with obesity include gestational diabetes mellitus and prediabetic conditions such as, elevated plasma insulin concentrations, impaired glucose tolerance, impaired fasting glucose and insulin resistance syndrome. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Also described herein, are methods of enhancing GLP-1 secretion in a mammal by administering, to a mammal, the compounds and pharmaceutical compositions described herein. The incretin hormone GLP-1 is believed to have several beneficial effects for the treatment of diabetes mellitus and obesity. GLP-1 stimulates glucose-dependent biosynthesis and secretion of insulin, suppresses glucagon secretion, and slows gastric emptying. Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Compounds that can enhance GLP-1 secretion are useful in improving insulin responsiveness in the liver, decreasing the rate of gluconeogenesis and glycogenolysis, and lowering the rate of hepatic glucose output resulting in a decrease in the levels of plasma glucose.

Administration

Any suitable route of administration may be employed for providing a mammal, especially a human, with an effective dose of a compound described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds described herein are indicated, generally satisfactory results are obtained when the compounds described herein are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. In some cases, the daily dose may be as high as 1 gram. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 15 mg, 20 mg, 25 mg, 30 mg, 40 mg, 50 mg, 100 mg, 200 mg, 250 mg, 300 mg, 400 mg, 500 mg, and 750 mg. Other oral forms may also have the same or similar dosages.

Compositions

Also described herein are pharmaceutical compositions which comprise a compound described herein and a pharmaceutically acceptable carrier. The pharmaceutical compositions described herein comprise a compound described herein or a pharmaceutically acceptable salt as an active ingredient, as well as a pharmaceutically acceptable carrier and optionally other therapeutic ingredients. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions as oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also optionally including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially two or more surfactants) will form emulsions or microemulsions on contact with water. The compound may also be formulated in a water soluble polymer in which it has been dispersed as an amorphous phase by such methods as hot melt extrusion and spray drying, such polymers including hydroxylpropylmethylcellulose acetate (HP-MCAS), hydroxylpropylmethyl cellulose (HPMCS), and polyvinylpyrrolidinones, including the homopolymer and copolymers.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant or mixture of surfactants such as hydroxypropylcellulose, polysorbate 80, and mono and diglycerides of medium and long chain fatty acids. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combinations

Compounds described herein may be used in combination with other drugs that may also be useful in the treatment or amelioration of the diseases or conditions for which compounds described herein are useful. Such other drugs may be administered, by a route and in an amount commonly used therefore, contemporaneously or sequentially with a compound described herein. In the treatment of patients who have type 2 diabetes, insulin resistance, obesity, metabolic syndrome, and co-morbidities that accompany these diseases, more than one drug is commonly administered. The compounds described herein may generally be administered to a patient who is already taking one or more other drugs for these conditions. Often the compounds will be administered to a patient who is already being treated with one or more antidiabetic compound, such as DPP-4 inhibitors, metformin, sulfonylureas, and/or PPAR agonists, when the patient's glycemic levels are not adequately responding to treatment.

When a compound described herein is used contemporaneously with one or more other drugs, a pharmaceutical composition in unit dosage form containing such other drugs and the compound described herein is preferred. However, the combination therapy also includes therapies in which the compound described herein and one or more other drugs are administered on different overlapping schedules. It is also contemplated that when used in combination with one or more other active ingredients, the compound described herein and the other active ingredients may be used in lower doses than when each is used singly. Accordingly, the pharmaceutical compositions described herein include those that contain one or more other active ingredients, in addition to a compound described herein.

Examples of other active ingredients that may be administered in combination with the compounds described herein, and either administered separately or in the same pharmaceutical composition, include, but are not limited to:

(a) dipeptidyl peptidase-IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators: (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) SSTR3 antagonists.

The above combinations include combinations of a compound described herein not only with one other active compound, but also with two or more other active compounds. Non-limiting examples include combinations of compounds described herein with two or more active compounds selected from biguanides, sulfonylureas, HMG-CoA reductase inhibitors of fructose 1,6-bisphosphatase, such as those disclosed in U.S. Pat. Nos. 6,054,587; 6,110,903; 6,284,748; 6,399,782; and 6,489,476;

(t) acetyl CoA carboxylase-1 and/or -2 inhibitors;
(u) AMPK activators; and
(v) agonists of GPR-119.

Dipeptidyl peptidase-IV inhibitors that can be combined with compounds described herein include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27, May 2004), Specific DPP-1V inhibitor compounds include sitagliptin (MK-0431); vildagliptin (LAF 237); denagliptin; P93/01; saxagliptin (BMS 477118); RO0730699; MP513; SYR-322: ABT-279; PHX1149; GRC-8200; and TS021.

Antiobesity compounds that can be combined with compounds described herein include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds described herein, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds described herein include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds described herein include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Suitable melanocortin-4 receptor (MC4R) agonists include, but are not limited to, those disclosed in U.S. Pat. Nos. 6,294,534, 6,350,760, 6,376,509, 6,410,548, 6,458,790, 6,472,398, 5,837,521, 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187963, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

EXAMPLES

Functional Assay to Assess the Inhibition of SSTR5Mediated Cyclic AMP Production:

The effects of compounds that bind to human and murine SSTR5 with various affinities on the functional activity of the receptor were assessed by measuring cAMP production in the presence of Forskolin (FSK) alone or FSK plus SS-28 in SSTR5 expressing CHO cells. FSK acts to induce cAMP production in these cells by activating adenylate cyclases, whereas SS-28 suppresses cAMP production in the SSTR5 stable cells by binding to SSTR5 and the subsequent inhibition of adenylate cyclases via an alpha subunit of GIP-binding protein (Gαi).

To measure the agonism activity of the compounds, human or mouse SSTR5 stable CHO cells were pre-incubated with the compounds for 15 min, followed by a one-hour incubation of the cells with 5 μM FSK (in the continuous presence of the compounds). The amount of cAMP produced during the incubation was quantified with the Lance cAMP assay kit (PerkinElmer, CA) according to the manufacturer's instruction, as well as, an $IC_{50}$ value was obtained by an eight-point titration.

| Example No. | Structure | R5 Bnd IC50 (nM) | cAMP IC50 (nM) |
|---|---|---|---|
| 19 | 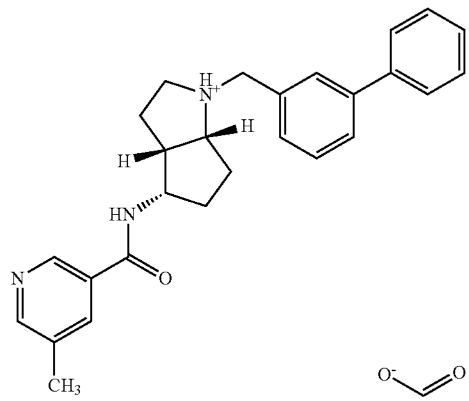 | 123.6 | 1217 |
| 60 | 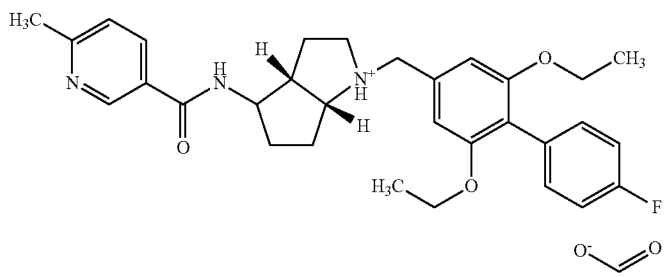 | 5.446 | 46.21 |
| 61 | 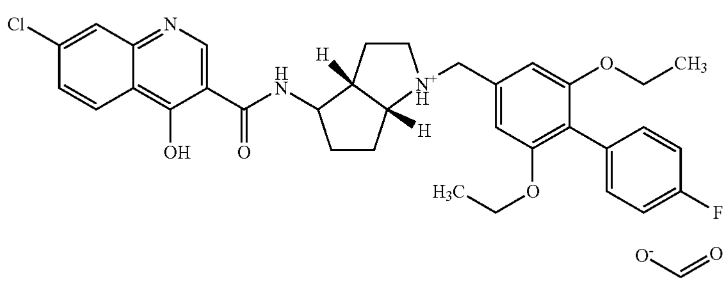 | 15.75 | 122.1 |
| 63 | 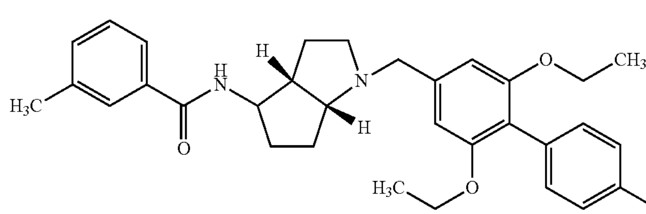 | 1.718 | 32.63 |
| 69 | 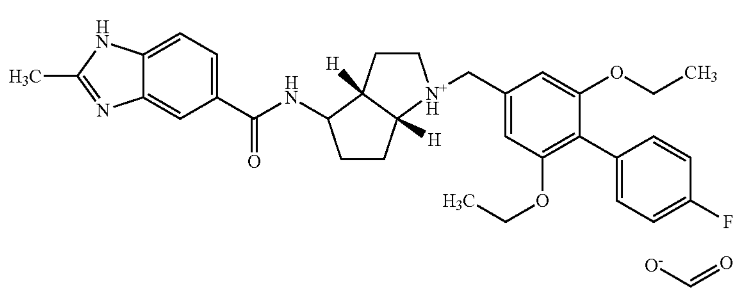 | 53.47 | 136.9 |

-continued
| Example No. | Structure | R5 Bnd IC50 (nM) | cAMP IC50 (nM) |
|---|---|---|---|
| 72 | 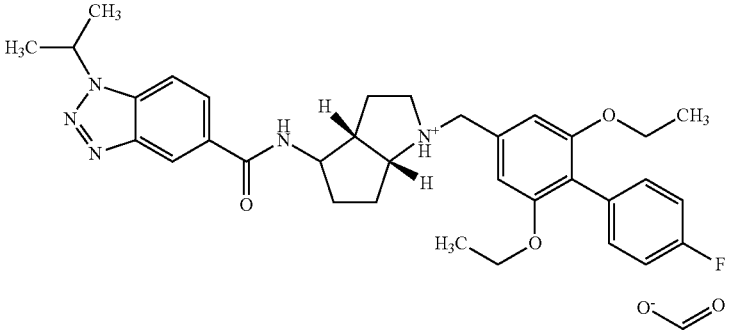 | 4.647 | 59.51 |
| 75 | 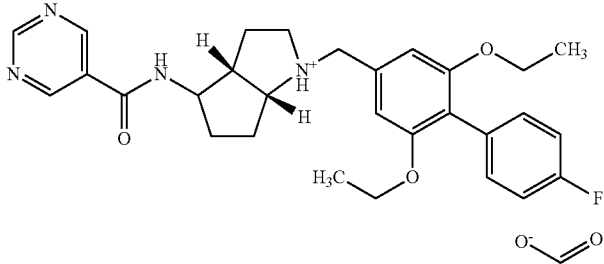 | 148.3 | 386.3 |
| 79 | 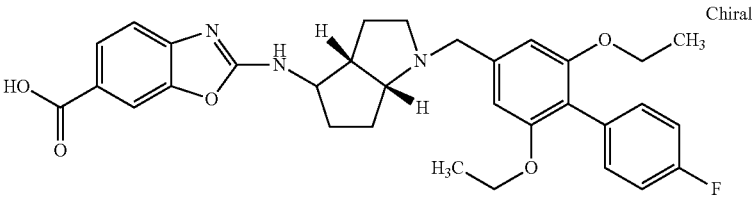 [SMILES: CCOc1cc(CN2CC[C@H]3C(Nc4nc5ccc(C(=O)O)cc5o4)CC[C@H]32)cc(OCC)c1-c1ccc(F)cc1] Chiral | 1.291 | 5.21 |
| 81 | 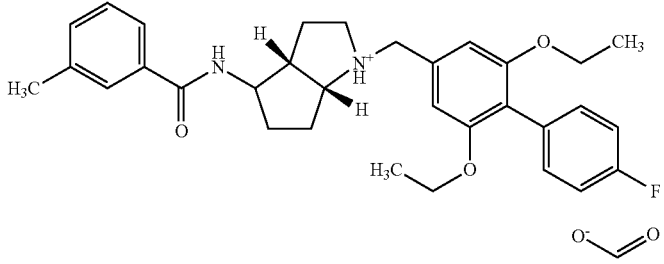 | 5.015 | 70.11 |
| 83 | 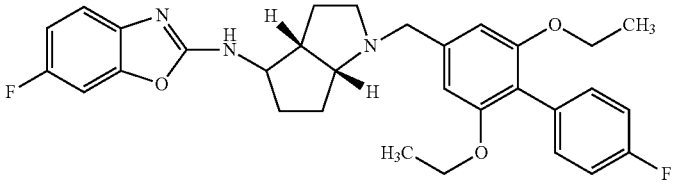 [SMILES: CCOc1cc(CN2CC[C@H]3C(Nc4nc5ccc(F)cc5o4)CC[C@H]32)cc(OCC)c1-c1ccc(F)cc1] | 7.47 | 252.1 |
| 90 | 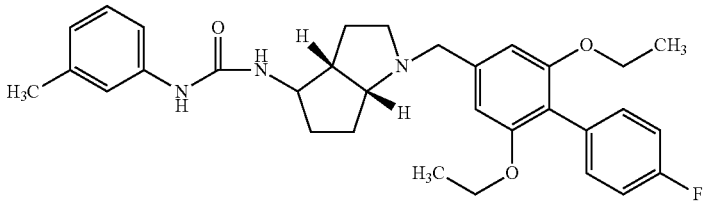 [SMILES: CCOc1cc(CN2CC[C@H]3C(NC(=O)Nc4cccc(C)c4)CC[C@H]32)cc(OCC)c1-c1ccc(F)cc1] | 4.994 | 85.72 |

-continued

| Example No. | Structure | R5 Bnd IC50 (nM) | cAMP IC50 (nM) |
|---|---|---|---|
| 97 | 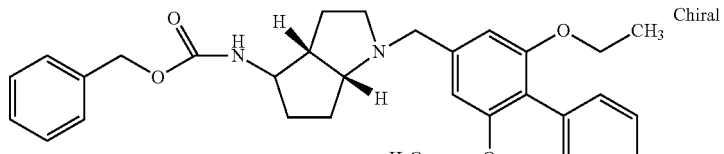 | 1.436 | 32.44 |
| 100 | 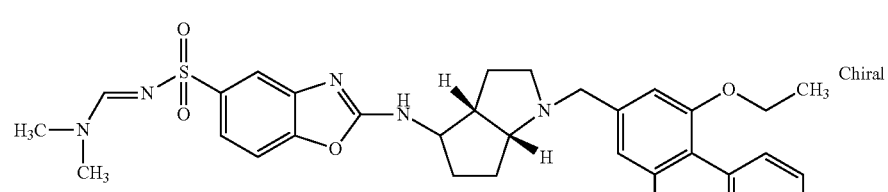 | 2.066 | 38.72 |
| 101 | 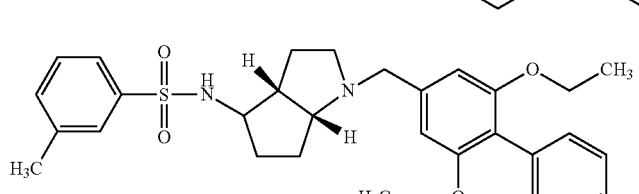 | 12.07 | 262.9 |

What is claimed is:

1. A compound of structural formula I:

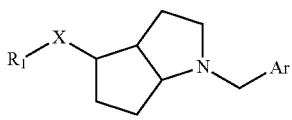

or a pharmaceutically acceptable salt thereof; wherein
Ar is an aryl or heteroaryl, wherein the aryl or heteroaryl are optionally substituted with one or more substituents independently selected from the group consisting of:
—$OC_{1-10}$ alkyl,
—$OC_{3-6}$ cycloalkyl,
—O-heteroaryl,
—O-aryl,
aryl,
aryl substituted with one to three halogen,
aryl substituted with one to three $C_{1-10}$ alkyl,
heteroaryl,
heteroaryl substituted with one to three halogen,
heteroaryl substituted with one to three $C_{1-10}$ alkyl,
halogen,
—$CO_2H$,
—$C_{1-10}$ alkoxycarbonyl,
—CN,
—$CF_3$,
$NH_2$,
pyrrolidone,
cycloheteroalkyl,
$C_{1-10}$ alkyl,
$C_{3-6}$ cycloalkyl, and
$C_{3-6}$ cycloalkyl substituted with one to three $C_{1-10}$ alkyl;
X is O, NH or $OCH_2$;
$R^1$ is $SO_2H$, $CONHC_{1-10}$ alkyl, —$C_{1-10}$ alkoxycarbonyl, aroyl, heteroaroyl, aryl, heteroaryl, cycloalkyl or cycloheteroalkyl wherein the $CONHC_{1-10}$ alkyl, —$C_{1-10}$ alkoxycarbonyl, aroyl, heteroaroyl, aryl, heteroaryl, cycloalkyl or cycloheteroalkyl are optionally substituted with one or more substituents independently selected from the group consisting of:
—OH,
—$OC_{1-10}$ alkyl,
—$OC_{3-6}$ cycloalkyl,
—O heteroaryl,
—O aryl,
aryl substituted with one to three halogen,
aryl,
aryl substituted with one to three $C_{1-10}$ alkyl,
heteroaryl,
halogen,
$SO_2C_{1-10}$ alkyl,
$SO_2$-aryl,
$SO_2$-aryl-$C_{1-10}$ alkyl,
—C(O)H,
—$C(O)C_{1-10}$ alkyl,
—$C(O)C_{3-6}$ cycloalkyl,
—C(O) cycloalkyl,
—C(O) heteroaryl,
—C(O) aryl,
—OC(O)H,
—$OC(O)C_{1-10}$ alkyl,
—$OC(O)C_{3-6}$ cycloalkyl,
—OC(O) cycloalkyl,
—OC(O) heteroaryl,
—OC(O) aryl, —NH₂,
CONH—C₁₋₁₀ alkyl-aryl,
—CONH₂,
—CO₂H,
—C₁₋₁₀ alkoxycarbonyl,
—CO₂C₁₋₁₀ alkylaryl,
—CN,
—CF₃,
—OCF₃,
—OCHF₂,
cycloheteroalkyl,
pyrrolidone,
C₁₋₁₀ alkyl-OH,
C₁₋₁₀ alkyl, and
C₃₋₆ cycloalkyl.

2. The compound or salt of claim 1, wherein Ar is phenyl.

3. The compound or salt of claim 1, wherein Ar is substituted with:
CO₂H,
—OC₁₋₁₀ alkyl,
aryl substituted with one to three halogen,
heteroaryl,
aryl,
aryl substituted with one to three C₁₋₁₀ alkyl,
C₁₋₁₀ alkyl, and
C₃₋₆ cycloalkyl.

4. The compound or salt of claim 1, wherein $R^1$ is aroyl or heteroaroyl.

5. The compound or salt of claim 1, wherein $R^1$ is heteroaryl.

6. The compound or salt of claim 1, wherein $R^1$ is substituted with:
—OC₁₋₁₀ alkyl,
halogen,
SO₂C₁₋₁₀ alkyl,
—NH₂,
—CONH₂,
—CO₂H,
—C₁₋₁₀ alkoxycarbonyl,
—CO₂C₁₋₁₀ alkylaryl,
—CF₃,
—OCHF₂,
C₁₋₁₀ alkyl-OH, and
C₁₋₁₀ alkyl.

7. The compound or salt of claim 1, wherein $R^1$ is selected from the group consisting of:

8. The compound or salt of claim 1 selected from the group consisting of:

9. A composition comprising a compound of claim 1 in combination with a pharmaceutically acceptable carrier.

10. A method of treating diabetes comprising administering to a patient in need thereof a therapeutic amount of a compound of claim 1.

11. A compound of structural formula Ia:

or a pharmaceutically acceptable salt thereof; wherein
$R^2$, $R^3$, $R^4$ and $R^5$ are independently selected from the group consisting of:
—OH,
—OC₁₋₁₀ alkyl,
—OC₃₋₆ cycloalkyl,
—O heteroaryl,
—O aryl,
aryl substituted with one to three halogen,
heteroaryl,
halogen,
—C(O)H,
—C(O)C₁₋₁₀ alkyl, —C(O)C$_{3-6}$ cycloalkyl,
—C(O) cycloalkyl,
—C(O) heteroaryl,
—C(O) aryl,
—OC(O)H,
—OC(O)C$_{1-10}$ alkyl,
—OC(O)C$_{3-6}$ cycloalkyl,
—OC(O) cycloalkyl,
—OC(O) heteroaryl,
—OC(O) aryl,
—CO$_2$H,
—C$_{1-10}$ alkoxycarbonyl,
—CN,
—CF$_3$,
—OCF$_3$,
—OCHF$_2$,
cycloheteroalkyl,
C$_{1-10}$ alkyl, and
C$_{3-6}$ cycloalkyl.

12. A compound of structural formula Ib:

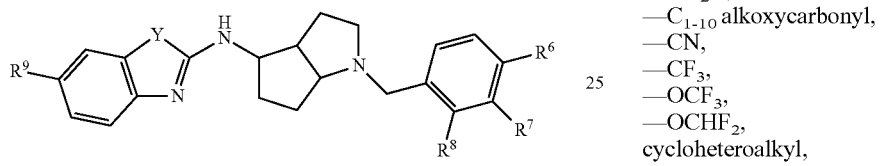

or a pharmaceutically acceptable salt thereof; wherein $R^6$, $R^7$, $R^8$ and $R^9$ are independently selected from the group consisting of:
—OH,
—OC$_{1-10}$ alkyl,
—OC$_{3-6}$ cycloalkyl,
—O heteroaryl,
—O aryl,
aryl substituted with one to three halogen,
heteroaryl,
halogen,
—C(O)H,
—C(O)C$_{1-10}$ alkyl,
—C(O)C$_{3-6}$ cycloalkyl,
—C(O) cycloalkyl,
—C(O) heteroaryl,
—C(O) aryl,
—OC(O)H,
—OC(O)C$_{1-10}$ alkyl,
—OC(O)C$_{3-6}$ cycloalkyl,
—OC(O) cycloalkyl,
—OC(O) heteroaryl,
—OC(O) aryl,
—CO$_2$H,
—C$_{1-10}$ alkoxycarbonyl,
—CN,
—CF$_3$,
—OCF$_3$,
—OCHF$_2$,
cycloheteroalkyl,
C$_{1-10}$ alkyl, and
C$_{3-6}$ cycloalkyl; and
wherein Y is O, S or N.

* * * * *